US008918305B2

(12) United States Patent
Bowers

(10) Patent No.: US 8,918,305 B2
(45) Date of Patent: Dec. 23, 2014

(54) DISTRIBUTED COMPUTATION OF MULTIPLE-BODY INTERACTIONS USING LOCAL-COORDINATE REFERENCE FRAMES

(75) Inventor: Kevin J. Bowers, Bridgewater, NJ (US)

(73) Assignee: D.E. Shaw Research, LLC, New York, NY (US)

( * ) Notice: Subject to any disclaimer, the term of this patent is extended or adjusted under 35 U.S.C. 154(b) by 1613 days.

(21) Appl. No.: 12/053,170

(22) Filed: Mar. 21, 2008

(65) Prior Publication Data

US 2008/0234990 A1 Sep. 25, 2008

Related U.S. Application Data

(60) Provisional application No. 60/896,675, filed on Mar. 23, 2007, provisional application No. 60/909,037, filed on Mar. 30, 2007.

(51) Int. Cl.
*G06G 7/48* (2006.01)
*G06F 19/00* (2011.01)
*G06F 17/50* (2006.01)
*G06T 17/20* (2006.01)

(52) U.S. Cl.
CPC .............. *G06F 19/701* (2013.01); *G06F 17/50* (2013.01); *G06T 17/20* (2013.01); *G06F 2217/16* (2013.01)
USPC .......................................................... 703/6

(58) Field of Classification Search
CPC ... G06F 2217/16; G06F 19/701; G06F 17/20; G06F 17/50
USPC ....................................................... 703/2, 6
See application file for complete search history.

(56) References Cited

U.S. PATENT DOCUMENTS

| 5,377,129 | A | * | 12/1994 | Molvig et al. | 703/9 |
| 5,424,963 | A | * | 6/1995 | Turner et al. | 703/6 |
| 5,432,718 | A | * | 7/1995 | Molvig et al. | 703/9 |
| 5,594,671 | A | * | 1/1997 | Chen et al. | 703/6 |
| 2005/0075849 | A1 | * | 4/2005 | Maher et al. | 703/2 |

FOREIGN PATENT DOCUMENTS

| WO | WO2006/113825 | 10/2006 |
| WO | WO2007/022469 | 2/2007 |

OTHER PUBLICATIONS

Shaw "A Fast, Scalable Method for the Parallel Evaluation of Distance-Limited Pairwise Particle Interactions," J. Comput. Chem. 26:1318-1328 2005.*
Bowers et al., "Scalable Algorithms for Molecular Dynamics Simulations on Commodity Clusters," Proceedings of the 2006 ACM/IEEE SC 06 Conference (13 pages).
David E. Shaw, "A Fast, Scalable Method for the Parallel Evaluation of Distance-Limited Pairwise Particle Interactions," J. Comput. Chem. 26:1318-1328 (2005) XP-002417446.
Bowers et al., "Overview of Neutral Territory Methods for Parallel Evaluation of Pairwise Particle Interactions," Journal of Physics: Conference Series 16:300-304 (2005).
Patent Cooperation Treaty, International Search Report for PCT/US2008/057853, mailed Nov. 18, 2008 (9 pages).

* cited by examiner

*Primary Examiner* — David Silver
(74) *Attorney, Agent, or Firm* — Occhiuti & Rohlicek LLP

(57) ABSTRACT

Distributed computation of multiple body interactions in a region uses multiple processing modules, where each of the processing modules is associated with a respective corresponding portion of the region. In some examples, the approach includes establishing multiple coordinate frames of reference, each processing module corresponding to one the coordinate frames of reference. In some examples, efficient techniques are used for selecting elements for computation of interactions according at least in part to a separation-based criterion.

23 Claims, 17 Drawing Sheets

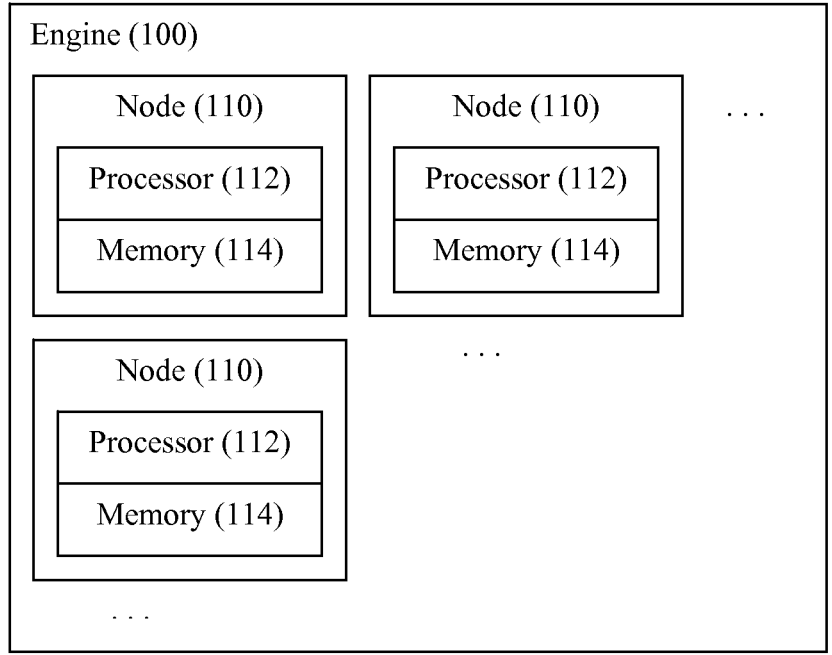

FIG. 1

$$\Phi = \Phi_{bonded} + \Phi_{non-bonded} + \Phi_{long-range}$$

with $$\Phi_{bonded} = \sum_{s \in \text{springs}} \tfrac{1}{2} k_s \left( \left| r_{i_s j_s} \right| - r_s \right)^2 + \sum_{a \in \text{angles}} \tfrac{1}{2} k_a \left( \theta_{i_a j_a k_a} - \theta_a \right)^2 + \ldots - \sum_{e \in \text{exclusions}} \frac{q_{i_e} q_{j_e}}{\left| r_{i_e j_e} \right|} \text{erf}\left( \beta \left| r_{i_e j_e} \right| \right)$$

$$\Phi_{non-bonded} = \sum_{i \in \text{particles}} \sum_{\substack{j \in \text{particles} \\ \text{such that } j<i, \\ |r_{ij}|<R_{non-bonded} \text{ and} \\ i-j \text{ are not excluded}}} \frac{A_{t_i t_j}}{\left| r_{ij} \right|^{12}} - \frac{B_{t_i t_j}}{\left| r_{ij} \right|^{6}} + \frac{q_i q_j}{\left| r_{ij} \right|} \text{erfc}\left( \beta \left| r_{ij} \right| \right)$$

$$\Phi_{long-range} = \sum_{i \in \text{particles}} \sum_{\substack{j \in \text{particles} \\ \text{such that } j<i}} \sum_{L \in \text{image shifts}} \frac{q_i q_j}{\left| r_{ij} + L \right|} \text{erf}\left( \beta \left| r_{ij} + L \right| \right)$$

FIG. 2

| Action | | Time | Cost |
|---|---|---|---|
| One flop (peak single precision) | | 0.1 ns | 1 |
| Data movement (32-bit) | L1 Cache | 0.1 ns | 1 |
| | L2 Cache | 0.2 ns | 2 |
| | Memory | 0.5 ns | 5 |
| | Internode | 5 ns | 50 |
| Data access (latency) | L1 Cache | 1 ns | 10 |
| | L2 Cache | 5 ns | 50 |
| | Memory | 50 ns | 500 |
| | Internode | 10 μs | 100,000 (!) |

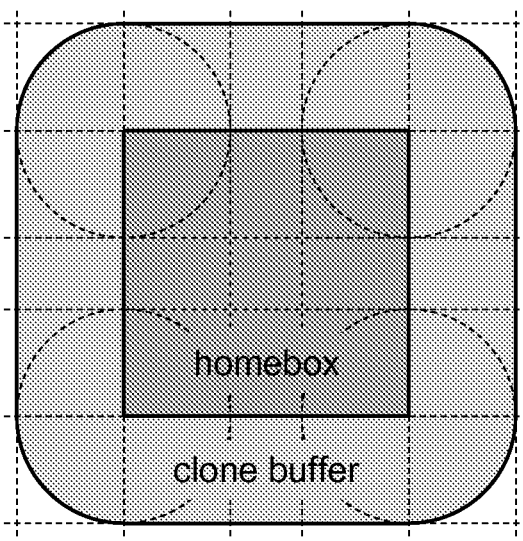
FIG. 5
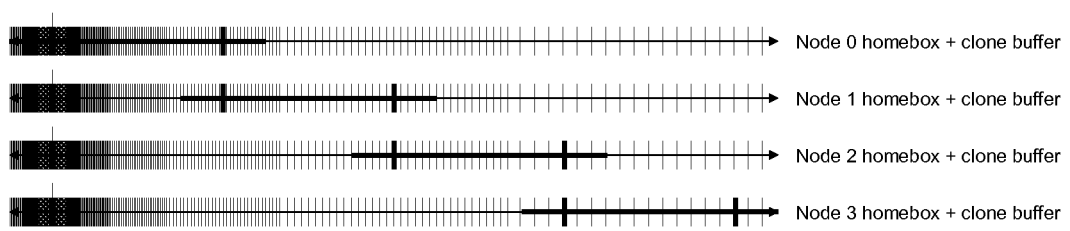
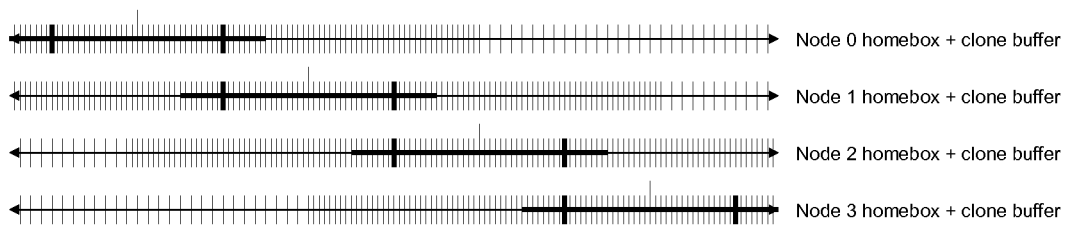
FIG. 6

(a)            (b)

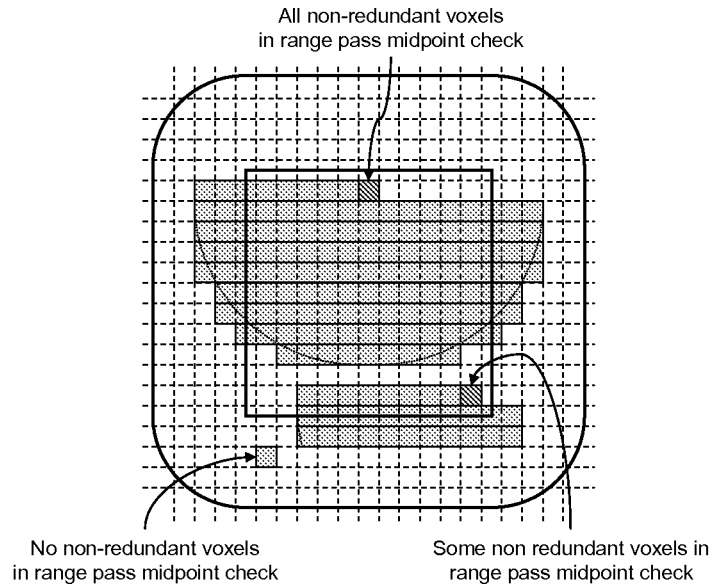

FIG. 24

```
p += f dt / 2 for all particles          p += f dt / 2 for local particles
x += p dt / m for all particles          x += p dt / m for local particles if time to assemble pairlist,            if time to assemble pairlist,
                                            migrate particles and bond terms
   assemble pairlist                        assemble local pairlist
end if                                   end if clear forces for all particles           clear local forces for local particles
reduce all bond terms to forces          reduce local bond terms to local forces
reduce all nonbonded terms to forces     reduce local nonbonded terms to local forces spread charge of all particles to mesh   spread charge of local particles to local mesh
k-mesh rho = 3d fft mesh rho             local k-mesh rho = distributed 3d fft local mesh rho
k-mesh phi = kernel .* k-mesh rho        local k-mesh phi = local kernel .* local k-mesh rho
mesh phi   = 3d ifft k-mesh phi          local mesh phi   = distributed 3d ifft local k-mesh phi
reduce mesh forces to all particles      reduce local mesh forces to local particles coalesce forces
                                         update forces p += f dt / 2 for all particles          p += f dt / 2 for local particles
```

FIG. 25

```
p += f dt / 2 for all particles
x += p dt / m for all particles
apply position constraints if time to assemble pairlist, assemble pairlist end if clear forces for all particles
reduce all bond terms to forces
reduce all nonbonded terms to forces spread charge of all particles to mesh
k-mesh rho = 3d fft mesh rho
k-mesh phi = kernel .* k-mesh rho
mesh phi   = 3d ifft k-mesh phi
reduce mesh forces to all particles p += f dt / 2 for all particles
apply velocity constraints
```

```
p += f dt / 2 for local particles
x += p dt / m for local particles
apply local position constraints if time to assemble pairlist,
   update positions and momenta
   migrate particles, bond terms and constraints
   assemble local pairlist
else
   update positions
end if clear local forces for local particles
reduce local bond terms to local forces
reduce local nonbonded terms to local forces spread charge of local particles to local mesh
local k-mesh rho = distributed 3d fft local mesh rho
local k-mesh phi = local kernel .* local k-mesh rho
local mesh phi   = distributed 3d ifft local k-mesh phi
reduce local mesh forces to local particles coalesce forces
update forces p += f dt / 2 for local particles
apply local velocity constraints
```

FIG. 26

```
for all particles to gather for "direction" in order,
   append particle position to the outgoing message
end for
```
(a)

```
for all particles to scatter for "direction" in order,
   remove position from the incoming message
   transform position into the local coordinate system
   save result in the local particle record
end for
```
(b)

FIG. 27

```
for all particles to scatter for "direction" in order,
   append the particle force to the outgoing message
end for
```

(a)

```
for all particles to gather for "direction" in order,
   remove force from the incoming message
   reduce force to the particle force
end for
```

```
let neighbor (nx,ny,nz)     = (nx+1) + 3*(ny+1) + 9*(nz+1) for nx,ny,nz in {-1,0,1}.
let [x,y,z]                 = local position of particle [rx,ry,rz]
let [one_dx,one_dy,one_dz]  = reciprocal clone buffer thicknesses ... compute the owner bits (relative index of the node that owns the particle) and
transform the position into the owner coordinate system.

bits = neighbor(0,0,0)
if x< -0.5, bits = bits - 1, x = x + 1, else if x>=0.5, bits = bits + 1, x = x - 1, end if
if y< -0.5, bits = bits - 3, y = y + 1, else if y>=0.5, bits = bits + 3, y = y - 1, end if
if z< -0.5, bits = bits - 9, z = z + 1, else if z>=0.5, bits = bits + 9, z = z - 1, end if
shift bits left 27

... compute the terms of the equations that describe the shape of the clone regions and
evaluate all the equations to set the "nodes with copy" status bits.

let term_x(-1,0,1) = [ ((x+0.5)*one_dx)^2, 0, ((x-0.5)*one_dx)^2 ]
let term_y(-1,0,1) = [ ((y+0.5)*one_dy)^2, 0, ((y-0.5)*one_dy)^2 ]
let term_z(-1,0,1) = [ ((z+0.5)*one_dz)^2, 0, ((z-0.5)*one_dz)^2 ]
for nx in {-1,0,1},
  for ny in {-1,0,1},
    for nz in {-1,0,1},
      if term_x(nx) + term_y(ny) + term_z(nz) < 1,
        set bit number neighbor(nx,ny,nz) in bits
      end if
    end for
  end for
end for
```

FIG. 29

```
clear local id next
for all particles in the cache in local id order,
   remove the particle global id to local id mapping from the octant maps
   compute new particle status bits and keep the old status bits for below
   if the particle is inbounds,
      if this node is the new owner,
         compute which neighbor nodes need but do not have a copy of the particle
         append a copy of the particle to the appropriate outgoing messages (the
            computed set of nodes serves as the particle store-forward multicast
            routing and is saved in the status bits of the outgoing copies)
      end if
      copy the particle to local id next
      increment local id next
   end if
end for
update the number of particles in cache to local id next
append the end-of-section delimiter to the outgoing messages
```

FIG. 30

```
for all particles in the current section of the incoming message,
   transform the particle position into the local coordinate system
   append a copy of the particle to the appropriate outgoing messages
   if the particle is needed here,
      recompute the new status bits for the particle
      append the particle to the local cache (resizing the local cache as necessary)
   end if
end for
advance the incoming message to the start of the next section
append the end-of-section delimiters to the remaining outgoing messages
```

FIG. 31

```
... Setup spatial queries.  This finalizes the local ids of the particles.

clear the voxel histogram
for all particles in the cache,
   update the particle voxel index
   update the voxel histogram
end for
convert the voxel histogram into a partitioning
make a copy of the partitioning
O(N) in-place sort cached particles by voxel using the partitioning and copy
for all voxels containing more than one particle,
   sort particles in the voxel by global id (ensures deterministic cache ordering)
end for ... Setup octant maps and gather / scatter patterns.

clear the gather / scatter patterns
for all particles in the cache,
   insert the particle global id to local id mapping into the appropriate octant maps
   append the particle local id to the appropriate gather / scatter patterns
end for
sort the gather / scatter patterns on the global id of the particles in the pattern,
   breaking ties based on position
```

FIG. 32

```
clear local id next
for all groups in the cache in local id order,
  compute the octant that contains the anchor point and save in the upper status bits
  convert the group particle local ids to global ids
  if this node is the current owner of the group,
    compute which neighbors need but do not have a copy of the group
    append copies of the group to the appropriate outgoing messages (the computed set
      of nodes serves as the group store-forward multicast routing and is saved in lower
      status bits of the outgoing copies; the local octant was saved in the upper
      status bits)
  end if
  if this node needs the group,
    copy the group to local id next (the local octant was saved in upper status bits)
    increment local id next
  end if
end for
update the number of cached groups to local id next
append the end-of-section delimiters to the outgoing messages
```

FIG. 33

```
for all groups in the current section of the incoming message,
  transform the octant in the group status bits into the local octant
  append a copy of the group to the appropriate outgoing messages
  if the group is needed here,
    append the group to the local cache (resizing the local cache as necessary)
  end if
end for
advance the incoming message to the start of the next section
append the end-of-section delimiters to the remaining outgoing messages
```

FIG. 34

```
for all groups in the cache,
   replace the group particle global ids with local
      ids using the particle octant map appropriate for the
      octant given in the group upper status bits
   set the group status bits to indicate which node is the
      owner and which nodes have a copy
end for
sort groups by global id, breaking ties by octant at low
   parallelism (ensures deterministic cache ordering)
```

FIG. 35

```
clear local pairlist
for all local particles i,
  for all local particles j with local id less than i,
    if i-j distance is less than cutoff,
        i-j midpoint is within homebox and
        i-j are not excluded
      append i-j to local pairlist
    end if
  end for
end for
```

FIG. 36

```
clear histogram array
for all exclusions in cache,
   i = exclusion local particle id of greater value
   increment histogram(i)
end for
convert the histogram into the i-partition array
copy i-partition array into temporary next array
for all exclusions in cache,
   i = exclusion local particle id of greater value
   j = exclusion local particle id of lesser value
   j-exclusion( next(i) ) = j
   increment next(i)
end for
```

FIG. 37

```
clear number of interactions, pairlist i-partition array and pairlist j-local id array
for all particles "i" in cache,
  append number of interactions to pairlist i-partition array
  for all exclusions with i in local exclusion pairlist,
    set bit number local id of excluded particle in exclusions bit field
  end for
  for all voxel ranges in pairlist template associated with voxel containing i,
    for all particles "j" in current voxel range,
      if i-j are not excluded,
         i-j are within cutoff distance,
         i-j have a midpoint in the homebox and
         i-j are not redundant,
        append local id of j to pairlist j-local id array
        increment number of interactions
      end if
    end for
  end for
  for all exclusions with i in local exclusion pairlist,
    clear bit number local id of excluded particles in exclusions bit field
  end for
end for
append the number of interactions to pairlist i-partition array
```

FIG. 38

DISTRIBUTED COMPUTATION OF MULTIPLE-BODY INTERACTIONS USING LOCAL-COORDINATE REFERENCE FRAMES

CROSS-REFERENCE TO RELATED APPLICATIONS

This application claims the benefit of the following U.S. applications:
U.S. Provisional Application No. 60/896,675 filed Mar. 23, 2007, and
U.S. Provisional Application No. 60/909,037 filed Mar. 30, 2007.

This application is related to the following International Applications, which are incorporated herein by reference:
Application PCT/US2005/023184, "EWALD SUMMATION METHOD FOR MOLECULAR SIMULATION," published on Jan. 12, 2006, as WO/2006/004877,
Application PCT/US2006/014782, "SCALABLE METHOD FOR THE EVALUATION OF DISTANCE-LIMITED PAIRWISE PARTICLE INTERACTIONS," published on Oct. 26, 2006, as WO/2006/113825, and
Application PCT/US2006/032498, "ARCHITECTURES FOR COMPUTATION OF PARTICLE INTERACTIONS," published on Feb. 22, 2007, as WO/2007/022469.

BACKGROUND

This invention relates to computation of particle interactions.

Computation of particle interactions arises, for example, in a molecular dynamics simulation. Such computations can be performed using a variety of hardware and/or software based system, which may be referred to as simulation engines. Some simulation engines make use of parallel computation using a moderate or large number of interconnected computation nodes, for example, using a general-purpose computer for each node interconnected using one or more data links or networks.

SUMMARY

In one aspect, in general, an approach to distributed computation of multiple body interactions in a region uses multiple processing modules, with each of the processing modules being associated with a corresponding portion of the region. A number of coordinate frames of reference are established. Each processing module corresponds to one of the coordinate frames of reference. Information for bodies in the region is maintained, including at each of the processing modules maintaining information for bodies in the portion of the region corresponding to the processing module according to the coordinate frame of reference corresponding to the processing module. At least some of the bodies have information maintained concurrently at multiple different processing modules according to different coordinate frames of reference.

This aspect may include one or more of the following features:

For each of a number of groups of bodies for which information for each of the bodies in the group is maintained at each of multiple processing nodes using multiple different coordinate frames of reference, a computation is performed that depends on locations of the bodies in the group resulting in an identical result at each of the processing modules. Performing the computation that depends on locations of the bodies can comprise evaluating a numerical inequality. Performing the computation that depends on locations of the bodies can comprise computing an interaction between the bodies.

Information for bodies in the portion of the region corresponding to a processing module is maintained according to the coordinate frame of reference corresponding to the processing module including using a representation of location information with a first spatial precision for bodies in the portion of the region associated with the processing module. The representation is such that it does not support the first precision for the complete region using a single coordinate frame of reference.

The representation comprises of an integer representation. This integer representation does not support representation of locations in the complete region using the coordinate frame of reference associated with the processing node. The representation can comprises a floating point representation with an exponent part and a fractional part. In some examples, the integer representation of location information uses the fractional part of the floating point representation.

Information for bodies is passed from a first of the processing modules to a second of the processing modules. The information for these bodies is maintained at the first processing module according to a first coordinate frame of reference. Passing the information includes transforming the information for the bodies from the first coordinate frame of reference to a second coordinate frame of reference for maintaining at the second of the processing modules.

A number of computations are performed, with each computation being associated with a group of bodies. Information for each of at least some of the groups of bodies is maintained at multiple of the processing modules. Performing the computation associated with the group of bodies includes selecting a single of the multiple processing modules for performing the computation by independently using information for the group of bodies maintained at each of the multiple processing modules.

In another aspect, in general, a method for selecting elements for computation of interactions is performed according to a separation-based criterion. Each element is associated with a spatial location in a spatial region, and the spatial region is partitioned into a plurality of parts of the region. A data representation of multiple tuples of parts of the region is stored. For each tuple there is at least one location in each of the parts that satisfies the separation-based criterion. A data representation is maintained for each of the parts of the region of those elements whose spatial location is in the part of the region. Tuples of elements are selected for computation. This selecting includes for each of the plurality of tuples of parts of the region, identifying tuples of elements, with each element of the tuple having a spatial location in a different part of the tuple of parts.

This aspect may include one or more of the following features:

Each tuple of parts of the region consists of a pair of parts of the region, and each tuple of elements consists of a pair of elements.

The data representation of the multiple tuples of parts of the region comprises, for each of the parts, a data representation of other parts that form pairs.

The separation based criterion comprises a maximum spatial separation of elements. In some examples, the separation based criterion further comprises a midpoint of the locations of the elements falling within a specified sub-region within the region.

A data representation of the tuples of parts of the region includes storing a data representation of those tuples of parts of the region from which for all tuples of locations with one location in each of the parts satisfy the separation-based criterion.

Identifying tuples of elements for computation includes testing at least some of the selected tuples of elements according to the separation-based criterion.

A data representation of excluded tuples of elements is stored. Identifying tuples of elements for computation includes determining whether tuples of elements are excluded tuples.

The data representation of elements whose spatial location is in the parts of the region is maintained by updating the data representation during an iterative computation while maintaining the data representation of the tuples of parts of the region as static.

Selecting tuples of elements for computation includes storing a data representation of the selected tuples. After selecting the tuples of elements, a computation is repeated for each of the selected tuples of elements.

The method is applied to computation of multiple body interactions in a simulation region. This includes storing and maintaining as static the data representation of the tuples of parts of the region prior to initiating a series of time iterations, and maintaining as dynamic the data representation for each of the parts of the region of elements whose spatial location is in the part of the region, wherein selecting the tuples of elements is performed at each of the time iterations.

In another aspect, in general, selecting elements for computation of interactions is performed according at least in part to a separation-based criterion. Each element is associated with a spatial location in a spatial region. A data representation of multiple tuples of elements for exclusion from selection is stored. The data representation includes an association between each of a number of first parts of tuples with a set of second parts of tuples, such that the combinations of the first parts and the second parts of the tuples form the tuples for exclusion from selection. Tuples for computation are selected by iterating over first parts of tuples, and for each first part of tuples, accessing the stored association of the first part of the tuples with the set of second parts of the tuples. Then, while iterating over second parts of the tuples selected according to the separation-based criterion, the second parts of the tuples represented in the accessed association are excluded from selection.

This aspect may include one or more of the following features:

Each tuple of elements consists of a pair of elements, and the first part of each tuple consists of a single element and the second part of each tuple consists of a single element.

The association between each of the first parts of tuples with a set of second parts of tuples comprises a Boolean vector. Each element of the vector is associated with a different one of a number of second parts of tuples, with the set of second parts of tuples being represented according to the values of the elements of the Boolean vector.

In another aspect, in general, computer-readable media is encoded with computer readable software comprising instructions for causing a processing system to perform all the steps of any of the above methods.

In another aspect, in general, a distributed data processing system is configured to perform all the steps of any of the above methods.

In another aspect, in general, an approach to computation of particles involves distributing computation to multiple processing nodes, with each node being associated with a portion of a spatial simulation region. Spatial information is represented at nodes such that different nodes use different coordinate frames of reference. For example, each node uses its own local coordinate reference frame.

This aspect may include one or more of the following features:

The frame of reference may be normalized. For example, the range of values may depend entirely or primarily on a predetermined range rather than on a spatial dimension associated with the portion of the simulation region associated with a node.

The frame of reference may be chosen such that the positions represented at a node are substantially balanced between positive and negative numbers.

Data for a same particle may be represented at different nodes using different reference coordinate systems.

Migration of a particle (e.g., transfer of data associated with a particle) from one node to another may involve transformation of spatial information from one coordinate system to another.

When using a toroidal simulation region (e.g., in a simulation using periodic boundary conditions), an advantage may include avoiding minimum image calculations during computation loops at the node. Another advantage may include avoiding periodic wrapping calculations. For example, by transforming coordinates as part of a process of transferring position information between node or as part of migrating particles from node to node (e.g., passing responsibility for or "ownership" of particles from node to node) nodes are not at an "edge" of a simulation region.

In another aspect, in general, elements (e.g., particles, groups etc.) represented in data structures at different nodes are identified by indices that are specific to each of the nodes. For example, the same particle may have a different identifier at different nodes at which it is represented.

Advantages can include simplified data arrangement in memory at a node, and simplified computation loops, for example, that allow sequential indexing over a range of indices.

In another aspect, in general, memory caches, which may be controlled through software procedures executing at a node, include compact arrangements of data that are used in computation loops executed at the node.

Indexing information for elements may be modified or computed as part of a migration or data distribution process between nodes.

Advantage can include efficient use of processor cache (e.g., as distinct from software controlled caches representing sets of elements) as a result of a relatively dense data structure and relatively regular access to the data structure. Other advantages can include possible arrangement of the cached data to provide efficient processing using vector of SIMD instructions on a node's processor.

In another aspect, in general, both a local coordinate system for spatial information and local indexing for elements are combined. For example, data may be queried by a combination of local id and local spatial region. In some examples, queries may additionally use global ids.

Multiple separate areas of memory can be used as separate caches for different types of records.

In another aspect, in general, data for elements (e.g., particles) are held at multiple nodes. For example, data for an element are held at a node that "owns" the particles (e.g., because the particle falls in the home box of the node) and data for that same particle may be held at neighboring nodes. In some examples, the nodes are arranged in a three-dimensional mesh and an element may be represented at a home node, and neighboring nodes in a 3×3×3 arrangement of nodes. A data structure representing a set of elements includes an indicator field for each element representing the neighboring nodes at which that element is also represented. In some examples, the indicator field is a bit-encoded field with each bit position indicating another node at which the element may be represented. For example, in a three-dimensional grid arrangement, each element may be represented at a subset of 3×3×3=27 nodes, and the 27 possible nodes correspond to 27 bit positions in an indicator field.

Advantages may include efficient processing of inter-node coordination routines. For example, determination of information to be communicated from one node to a neighboring node may involve looping over an array of elements testing a bit pattern (or patterns) in the indicator field for each element.

In another aspect, in general, identification of a set of pairs (or more generally tuples) of elements that satisfy a separation-based criterion makes use of a partition of a simulation space into regions (e.g., "voxels") and an identification of pairs (or more generally tuples) of regions (voxels) such that all pairs of elements that satisfy the criterion are found in at least one corresponding pair of identified regions (voxels) and pairs of elements that are found in a pair of regions (voxels) not identified are known not to satisfy the criterion.

This aspect can include features including determining specifications of the voxels and the identification of the pairs of voxels prior to multiple time steps of a simulation.

During a simulation, elements may be added and/or removed from the voxels, while the identified set of pairs of voxels remains static.

Construction of an element pairlist can involve iteration over identified pairs of voxels, and for each identified pair of voxels, iteration over pairs of elements with each element in the pair being from a corresponding voxel of the identified pair. The iteration over pairs of elements can involve further testing to determine whether the criterion is satisfied.

The separation-based criterion can include a maximum separation between the elements.

In another aspect, in general, an approach to iteration over pairs of elements excluding a specified set of pairs (or more generally n-tuples) (e.g., an exclusion list) involves an outer iteration over elements (i) (more generally (n−1)-tuples). Prior to iteration over candidate elements (j) to form pairs (i,j), a data structure representing a set of excluded pairs $\{(i,k)\}$ is constructed. In some examples, this data structure is represented as a bit vectors with each bit position corresponding to a different value of k.

Aspects can include one or more of the following features.

Associating each computation node with a unique non-overlapping region of space ("homebox"). The union of the homeboxes forms the simulation volumes.

Associating each homebox with a number of bi-directional communication links to nearby homeboxes.

Associating each homebox with a local coordinate system in which the homebox shape can be described simply and in which the conversion between two representations of a position in the vicinity of two homeboxes is computationally efficient (e.g., adding and subtracting by one, and/or can be performed without conditional branching in a sequence of processor instructions) and reversible.

Associating each homebox with a midpoint method compatible region surrounding that homebox ("clone buffer"). In some examples, a node associated with a homebox includes data representations of elements that are located in that region surrounding the homebox.

Assigning to a node only calculations that involve positions near or within the node's homebox or clone buffer.

Elimination of minimum image calculations from code. For example, use of local coordinate representations can be used in an approach to eliminate minimum image calculations.

Elimination of periodic wrapping calculations from code. For example, use of local coordinate representations can be used in an approach to eliminate periodic wrapping calculations.

A hybrid floating point/fixed point position representation is used.

The hybrid representation may be used to be performed bit level exact on nodes in the vicinity of nearby points. An advantage can include reducing need for communication.

A local representation of position may use a representation of sign to increase the absolute resolution of positions.

A hybrid floating point/fixed point position representation may be used to improve resolution as number of nodes for a simulation increases.

A hybrid floating point/fixed point position representation may be used to improve absolute resolution in worse case and typical case as compared to more traditional representations.

A hybrid floating point/fixed point position representation may be used to allow dynamic reconfiguration of position resolution without loss of performance.

A hybrid floating point/fixed point position representation may be used to allow for reversible and/or lattice dynamics simulations to be performed.

A hybrid floating point/fixed point position representation may have an advantage of increasing processing speed as compared to use of mixed integer/floating point code.

A hybrid floating point/fixed point position representation may be used to achieve round-to-even behavior efficiently without performance degradation.

Use of data records that identify which simulation entity they describe (e.g., use of global identifications).

Storing only data records needed for computations that may be assigned to a node in local managed software caches at that node.

Storing cached records in a uniquely determined order to avoid irreversibility in computations using the cache. For example, an explicit step of ordering the records may be used, or as another example the system uses an implicit ordering that guarantees reversibility.

An array of structures data layout is used for cached data, which may have an advantage of improving spatial and temporal data locality in computations using the cached data.

Caches are stored contiguously, which may have an advantage of allowing use of high performing streaming memory operations in calculations using the cache data.

Caches records are stored in an address alignment that is compatible with vectorized SIMD operations. This may have an advantage of increasing processing speed using data in the cache for example by when SIMD and/or vector operations use the cache.

Using similar record data layouts in caches for different types of elements, which may have an advantage of permitting use of low level communication routines, for example, for passing the records between nodes.

Status bits are stored in data records in a cache, for example, along with information in the data records, which may have an advantage of allowing records to be efficiently distributed to only nodes that need them during migrate operations according to the stored status bits.

Local coordinate system are used with signed hybrid floating point/fixed point representation for particle positions.

Local particles ids are used in group records (outside migrate), which may have an advantage of avoiding extra indirection in computations using these records and to avoid potentially complex minimum image calculations.

The data in the caches may be arranged (e.g., ordered) for efficient access to the records.

A cache may be arranged for O(1) selection of records with a range of positions in the cache.

A cache may be organized for O(1) selection of all records in cache that describe a particular simulation entity.

A cache may be organized for O(1) selection of records whose associated position is within a region space.

Octant maps are used to permit multiple copies of a record that describe a particular simulation entity to be present in a local cache.

Octant maps are used to allow for the determination of an appropriate set of compatible particle images for a group of particles in O(1) operations.

A homebox and clone buffer of a node are divided into a voxel mesh. Data records may be organized by voxel. For example, a cache is partitioned by voxel, which may have an advantage of facilitating spatial region queries.

A staged communication pattern is used to distribute data to neighbor nodes. For example, the staged pattern includes six data exchanges to distribute data to all 26 nearest neighbors (26=3×3×3−1) in migrate and update operations.

A time reversible communication pattern is used, for example, in coalesce operations.

Communications for different local sets of cached records are fused into a single execution of the basic communication pattern (or its time reverse).

Communication pattern message processing is overlapped with communication pattern execution.

One instance of a communication pattern execution is overlapped with a subsequent instance of a communication pattern execution.

A cache is associated with a "migrate begin" function. For example, the migrate begin function computes how to embed all the communications necessary for the locally cached records into a single execution of the basic communication pattern and appends records to outgoing migration messages accordingly.

A cache is associated with a "migrate receive" function. For example, the migrate receive function processes received migrate messages. The processing can include storing and forwarding received records accordingly.

A cache is associated with a "migrate end" function. For example, the migrate end function organizes the particle cache and updates all data structures.

Migrate messages are divided into sections each consisting of packed records followed by an invalid global id delimiter. These sections are appended by the "migrate begin" and "migrate receive" functions.

A single pass is used to compute all communications necessary, for example, for a migration between time steps of a simulation. For example, the bulk of all six migrate messages is assembled in "migrate begin" processing.

Group "migrate begin" functions are performed before a particle "migrate begin" functions.

Group "migrate end" functions are performed after particle "migrate end" functions. An advantage can be to allow group migrate functions to operate on a consistent particle caches at all times.

Use of record status bits to embed the store-forward multicast routing of records in the basic communication pattern.

Use of nearest neighbor communication restriction to reduce parallelization overhead while retaining high scalability via the midpoint method.

Use of pre-computed time-reversible gather/scatter patterns that embed store-forward multicast updates of particle records shared by several nodes into the basic communication pattern.

Use of callbacks during update and coalesce message assembly to allow custom application update and coalesce operations with minimal bandwidth and no formatting overhead to be performed.

Association of each particle with one and only one "owner" node.

Restricting particle displacement to less than a clone buffer thickness (and restricting clone buffer thickness to only overlap homeboxes on nearest neighbor nodes) ensures a particle record on a node at most only needs to be sent nearest neighbor nodes.

Use of 5 particle status bits to encode the relative nearest neighbor that owns a particle record.

Use of 27 particle status bits to encode which neighbors have a copy of a particle record. For example, the status bits are relative to the current node. As another example, the status bits are relative to the node that owns the particle.

Use of the home box owner regions and clone regions to rapidly compute new status bits during migrate.

Use of easily computably common functional forms to describe rounded clone region shapes.

Use of new and old particle status bits to allow a node to make decisions regarding cached particle records (e.g., a decision of whether to communicate information for those particles) with simple bit operations.

Transforming particle positions into the local coordinate system as records are received.

Use of an incremental migrate procedure such that the number of records sent during migrate scales substantially as the clone buffer exterior surface area. In some examples, no records are sent at all if particles have not moved since last migrate.

Space and time scalable updating all query data structures for the local element caches.

Storing the final local ids of particles within gather/scatter regions associated with a node at time of migrate such that nodes agree on the set of particles in matching gather/scatter patterns.

Sorting the local ids in the gather/scatter patterns by the associated particle global id and/or position to ensure a consistent ordering of particles in matching gather/scatter patterns.

Implicitly associating each group record with a position analogous to the position of a particle record.

Requiring that all particles in a group are no further than, at most, a clone buffer thickness of the anchor point to no computation or communication is necessary to ensure the a compatible set of particles for a group are present on at least one node.

Requiring the anchor point move less than a clone buffer thickness between migrations (and restricting the clone buffer to overlap only homeboxes of nearest neighbors) to insure that group records need only be communicated with nearest neighbor nodes during migrate.

Requiring the anchor point move less than half a homebox thickness between migrations to insure a trivial mapping of the octant that contains the anchor point on the owner immediately before a migration and any neighboring node to which the group record may be sent during migration.

Storing the group record on the node that owns the midpoint of the group (or an approximation of the midpoint) at time of last migration ("midpoint policy").

Storing a copy of the group record on a node for every complete compatible set of particles in which at least one particle is owned by the node ("replicate policy").

Storing the group record on the node that owns the first particle in the group at time of last migrate ("anchor policy").

Storing a copy of the group record on a node for every complete compatible set of particles present on that node ("ensured policy").

Use of new and old group status bits to allow a node to make decisions regarding cached group records with simple bit operations.

Use of an incremental group migrate policies (similar to the incremental particle cache policies) to reduce on migrate data volume. For example, no group records are communicated if particles have not moved.

Representing a group by particle global id and octant that contains the anchor point during the migrate as particle local ids are reassigned during migrate and the local id of a particle on one node has no relationship to the local ids of particles on neighboring nodes.

Transforming octant that contains the anchor point to the local octant when receiving a group.

Use the particle octant map to rapidly map a group from global particle ids to a compatible set of local particle ids at end of migration.

Space and time scalable updating all group record query data structures.

Use of a midpoint method compatible clone buffer to permit assembly of the local portion of the pairlist without communication and to permit subsequent calculations to use the pairlist with need for additional communication.

Use of a midpoint test during local pairlist assembly to insure that each nearby pair is assigned to one and only one node and to avoid needing the test midpoint in computations using the local pairlist.

Use of a local pairlist template to dramatically reduce the number of candidate pairs tested during local pairlist construction.

Storing all pairs of voxels that have (or may potentially have based on the location and geometry of the voxel regions) at least one pair of particles within the cutoff distance and at least one pair of particles that satisfy the midpoint check in the pairlist template.

Organizing pairs of voxels commensurate with the organization of a pairlist.

Compression of voxels paired with a given voxel into runs in the local pairlist template. An advantage may include reducing data volume requirements during local pairlist assembly.

Storing pairlist template to permit O(1) selection of all runs of voxels paired with a given voxel during local pairlist assembly.

Use of the group midpoint policy to ensure a node only caches the minimum set of proper compatible image exclusions it needs during local pairlist construction.

Use of the group ensured policy to ensure a node only caches the minimum set of proper compatible image exclusions it needs during dynamic load balanced local pairlist construction.

O(Nlocal) conversion of locally cached exclusion groups into an exclusion pairlist to permit O(1) selection of non-redundant particles locally excluded from a given particle during local pairlist assembly.

Use of O(1) selection of all local non-redundant exclusions for a given particle during local pairlist assembly.

Unpacking the set of non-redundant particles excluded from a given particle into a bit field to permit exclusions to be detected with an O(1) bit test in the inner loop of pairlist assembly.

Use of O(1) selection of all voxels runs needed for a given voxel during local pairlist assembly.

Use of O(1) selection of particles in a voxel run during local pairlist assembly.

Use of O(1) bit test in the loop during local pairlist construction.

Other features and advantages of the invention are apparent from the following description, and from the claims.

DESCRIPTION OF DRAWINGS

FIG. 1 is a block diagram.
FIG. 2 is an equation.
FIG. 5 is two-dimensional representation of a homebox with a clone buffer.
FIG. 6 is a diagram that illustrates one-dimensional comparison of position representations.
FIG. 24 is a two-dimensional representation of locations in pairlist templates
FIG. 25-FIG. 38 are listings of procedures.

DESCRIPTION

Figures 3, 4:
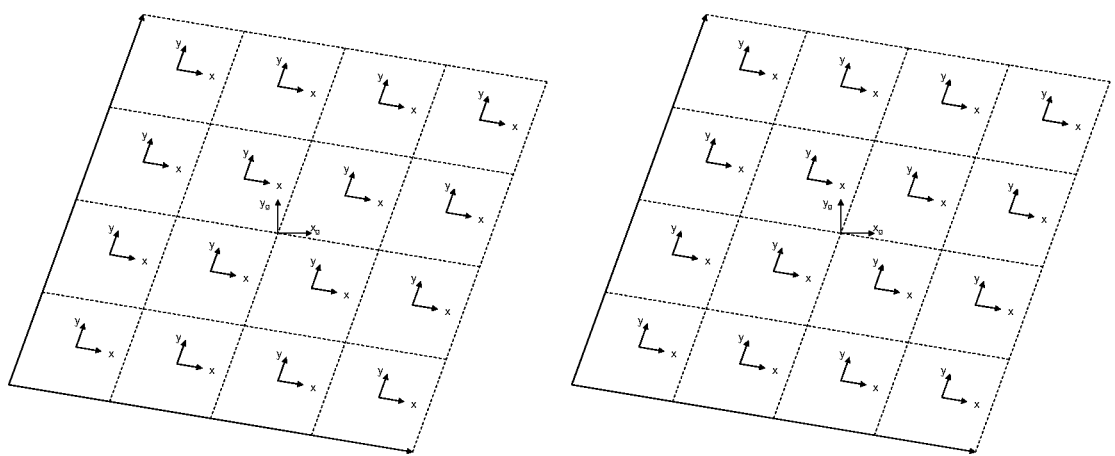
FIG. 3 is a table of performance characteristics.
FIG. 4 is a two-dimensional coordinate representation of homeboxes.

As shown in FIG. 1, a system 100, which may be referred as a "simulation engine" or simply "engine," is configured for performing computations related to particle interactions. In some examples, the system is used to implement an application for performing computer simulations of dynamic interactions in a molecular simulation. That is, the software application makes use of services of the simulation engine, with the simulation engine implementing relatively generic computation and communication tasks required by the application.

The system makes use a collection of nodes 110, each of which has one or more computer processors 112 (each of which may contain several processing "cores") and a memory 114. In some examples these nodes comprise general-purpose computers that are coupled by one or more data links or networks (not illustrated). The system is configured to process simulated particle interaction in a simulation volume.

In some examples described in this document, the engine uses hierarchical cache-like policies based on a midpoint method to parallelize particle simulations. The engine distributes particles and records that specify properties of sets of particles among computational nodes, assembles messages sent between computational nodes, manages ordering of data in memory, provides support finding pairs of nearby particles and provides support for massively parallel fast Fourier transform (FFT) computations. Implementations of the system can have one or more of the following properties: (1) inter-node messages are as small as possible, including only data that needs to be updated on other nodes; (2) no more messages are sent than necessary; (3) data is organized for efficient access in computations; (4) message assembly and data organization require minimal overhead; (5) codes using the engine do not need to perform low level communications or parallel bookkeeping and require minimal algorithmic alterations from their serial counterparts; (6) it is possible to efficiently detect and/or prevent violations of parallelization restrictions at run-time and (7) it is possible to build deterministic (and even bit-level time reversible) parallel codes on top the engine.

In some embodiment of the system, throughout a series of time steps of a simulation, data is distributed to each computational node such that each node has all the data needed to perform computations assigned to it. This data is arranged in an efficient order on the node. The system coordinates all inter-node communications, for example, in a distributed manner in which each node determines what data it holds that is needed by other nodes and distributes such data to those nodes during a simulation.

One application of the system is for the parallelization of all-atom explicit-water biochemical molecular dynamics simulations with long range electrostatics, which is an example of a type of problem referred to as "MD simulation." MD simulations, in general, use simultaneous parallelization of several different types of computations, including a small somewhat irregular static set of interactions between specific groups of nearby particles, a large dynamic set of interactions between arbitrary pairs of nearby particles, a large dynamic set of interactions between particles and a regular mesh, and fast Fourier transforms (FFTs). As similar computations occur in other kinds of particle simulation, the engine is generic and can be used for other disciplines, including plasma and astrophysics simulation, particle based hydrodynamics simulation and materials science simulation.

To better understand the engine methods and design of embodiments of the system that are described in this document, an overview of certain aspects of MD simulation is provided here without intending to limit the scope of what is claimed. In some implementations of MD simulation, the trajectory of all particles is computed with a sequence of discrete steps. In an MD simulation time step, the force acting on each particle (equal to the negative potential gradient at the particle position) is evaluated and the particle position and momentum are updated accordingly, perhaps with constraints to ensure relationships like bond lengths are satisfied throughout the simulation. The dominant computational expense of a MD step is evaluating the forces. The MD potential usually has the following form shown in FIG. 2. In FIG. 2, $r_{ij}$ gives the minimum image vector from particle i to particle j and $\theta_{ijk}$ gives the angle between $r_{ij}$ and $r_{kj}$. The remaining parameters describe the chemical system and approximations, for example chemical bonds, particle charges, van der Waals radii, boundary conditions, Ewald electrostatic splitting, and a non-bonded cutoff radius. $\Phi_{long-range}$ is written with a double sum over particles and a sum over all images for clarity. It is usually computed via much faster methods that exhaustive enumeration, for example, using Fourier Transform based techniques (e.g., s-PME, smooth Particle Mesh Ewald, and k-GSE, k-Gaussian Split Ewald). Physically, $\Phi_{bonded}$ represents the effect of covalent bonds between particles. Since fast long range algorithms like s-PME and k-GSE cannot exclude interactions between arbitrary sets of particle pairs in $\Phi_{long-range}$, long range interactions inadvertently computed between covalently bonded particles are explicitly subtracted in the last sum of $\Phi_{bonded}$. $\Phi_{non-bonded}$ represents the effect of short range interactions between particles that do not directly interact via covalent bonds. $\Phi_{long-range}$ represents long range electrostatic interactions between particles (including periodic boundary conditions). For clarity of exposition, $\Phi_{long-range}$ has been written as an $O(N^2)$ double sum over all particles and a sum over all images. However, this is typically computed using much faster approximate algorithms such as s-PME and k-GSE.

In Fourier based methods such as s-PME and k-GSE, a smooth charge density sampled on a regular mesh is computed from the particles ("charge spreading"). The charge density is convolved with the long range electrostatic Green's function by Fourier techniques (i.e., Fourier transform the smoothed particle density, array multiply the Fourier transformed charge density with the appropriate kernel and inverse Fourier transform the result) to yield the effective long range potential sampled on the mesh. Energies and gradients are interpolated from the mesh to the particles to complete the calculations of $\Phi_{long-range}$ ("force interpolation").

There are typically tens of thousands of particles in a MD simulation and the overall computational expense is roughly proportional to the number of particles. There are, in a given force calculation, typically 1 to 2 bond terms per particle (each takes roughly 20-200 operations to compute) and 150 to 400 non-bonded terms per particle (each takes roughly 50-100 operations to compute). Each particle interacts with 50 to 250 mesh points, each with its own term (each takes roughly 20 operations to compute). The number of mesh points scales roughly as the number of particles. Usually, in reference to the number of operations, the non-bonded terms are the most expensive computations and bond terms the least expensive computations. 1 to 2 bond terms per particle corresponds roughly to a 3 particle water molecule with 1 water constraint and 3 long range exclusions. 150 to 400 non-bonded terms per particle corresponds to a non-bonded cutoff distance of between 9 Å to 13 Å. 50 to 250 mesh points per particle corresponds to a PME order of between 4 and 6.

Because water is incompressible and MD simulations tend to be water dominated, the particles are usually approximately uniformly distributed throughout the simulation volume. As each bond and non-bonded term is associated with a set of nearby particles, it is useful to think of these terms having a "location" at the center of the smallest sphere that contains all the associated particles (or at the "midpoint"). By this metric, non-bonded terms tend to be approximately uniformly distributed throughout the simulation volume while bond terms have a more complicated distribution (solute regions like protein tend to have a higher density of computationally expensive bond terms). Mesh points and mesh-particle interactions are generally distributed uniformly throughout the simulation volume.

Resolving relevant timescales can require billions of sequential MD steps. For the sake of specificity in an example, and not as a limitation, this description refers to a modest sized MD simulation of a cubic periodic region with a volume of $(80 \text{ Å})^3$ containing approximately 51,000 particles and a non-bonded cutoff distance of 10 Å as a characteristic MD simulation. For parallelization, in some embodiments, nodes use two recent dual core processors (e.g., Intel x86 architecture processors) and Infiniband interconnect as a characteristic commodity node. The relative cost of various actions on such a node is shown in FIG. 3 as a table of performance characteristics of a characteristic commodity cluster node. These are "rule-of-thumb" figures. For reference, the inter-node figures correspond to a approximately 10 µs end-to-end latency with approximately 10 Gb/s interconnect and the flop operation corresponds to an x86 single precision SSE (Streaming SIMD Extension) operation at 2.5 GHz. Other figures were extracted from various commodity processor benchmarks and datasheets.

For a single core, it takes approximately 0.5 s to perform an MD step in the characteristic simulation. To parallelize this effectively over 1,024 cores in a cluster of characteristic nodes, the exposed communication time and parallel overhead per MD step should be better than 0.5 s divided by 1,024 cores, or approximately 500 µs. Exposed inter-node latency is an optimization priority. Massively parallelizing the characteristic MD simulation yields a budget of tens of exposed inter-node latencies per typical MD step. At the same time, there are only tens of particles per core and the influence of several hundred particles in the vicinity of each particle must be aggregated to compute the potential gradient at the particle.

Additionally, in isolation, optimal parallelization strategies for $\Phi_{bonded}$, $\Phi_{non-bonded}$ and $\Phi_{long-range}$ are generally different. The computation of $\Phi_{bonded}$ involves interactions between fixed groups of nearby particles for the simulation duration and thus ideally is parallelized with an a priori partitioning of terms (e.g., a balanced graph partition). The set of interactions involved in computing $\Phi_{non-bonded}$ is dynamic and involves rapidly finding pairs of nearby particles and testing them for exclusion. Since frequently re-computing the non-bonded term partition is non-trivial and since these terms are approximately uniformly distributed throughout the simulation volume anyway, spatial domain decomposition is preferred here. Likewise, the charge spreading and force interpolation steps in s-PME and k-GSE involve interactions between uniformly distributed particles and nearby uniform regular mesh points. This too is nominally parallelized by spatial domain decomposition. However, a FFT computation of a spatially decomposed mesh requires completely different long-range communication patterns and is very expensive in communications, though cheap in computation. In short, to compute a long sequence of MD steps massively parallel is extremely difficult. The engine makes it possible to do this, even in regimes like this, on commodity hardware.

Embodiments of the engine can provide 3 capabilities to applications that use it:
(1) Distribution of information regarding particles and small groups of particles among nodes ("migrate");
(2) Synchronization of select portions of particle data between nodes ("update" and "coalesce");
(3) Finding all non-excluded nearby particle pairs and assigning to nodes ("assemble pairlist").

The engine can also provide facilities for computing massively parallel FFTs, for integrity checking the parallel distribution of data, and for handling various computations involved with triclinic periodicity.

To understand how these above capabilities are used by an application, serial and engine parallelized versions of an unconstrained NVE (constant particle number, constant volume and constant energy) velocity Verlet MD step are shown side-by-side in FIG. 25. FIG. 25 presents a line-by-line comparison of the two procedures. The parallel version uses replicated particle integration. Engine operations that have no serial equivalent are marked in bold. Outside of these nearest neighbor synchronization operations, code using the engine in general is identical to the serial equivalent and does not need to perform any communications or parallel bookkeeping. Note that no barriers or reductions are required to perform this basic step. In general, the engine does not require applications to perform any barriers. For completeness, a side-by-side comparison of a constrained NVE velocity Verlet MD step (RATTLE) is shown in FIG. 26. Actions with no serial equivalent are marked in bold. This uses replicated constraint calculations and assumes each particle is in at most one small non-overlapping group of constraints. Since not all nodes with a copy of a particle are capable of performing constraint calculations involving that particle, an extra round of communications to keep nodes in sync is required per step over the unconstrained step. Active synchronization of data is minimized. As can be seen, the serial and parallel implementations are virtually identical. Steps outside the engine are trivially related to their serial counterparts. The engine performs all communications and parallel bookkeeping and the engine does not impose the need for any global synchronization in applications using it.

Some embodiments of the engine use a midpoint method as a parallelization strategy. In the midpoint method, interactions between particles are assigned to the node responsible for the region of space that contains the interaction "midpoint" (for example, the center of the smallest sphere that contains all the interacting particles). As a result, a node need only communicate with neighbors responsible for points no further away than the maximum possible distance between a particle in an interaction and the corresponding interaction midpoint. The midpoint method allows for a massive reduction in number of communications while still permitting scalability to tens of thousands of cores. For example, operations like migrate, update and coalesce in the characteristic MD simulation can be parallelized up to 4,096 characteristic nodes (16,384 cores) before needing more than nearest neighbor communications (a 10 Å non-bonded cutoff distance gives a 5 Å maximum distance to the midpoint). Further, because communications with nearest neighbors are usually sufficient, communications and parallel bookkeeping can be dramatically reduced and encapsulated separately into the engine.

Thus, the engine operations of migrate, update and coalesce usually require only a single round of nearest neighbor communications. In some embodiments of the engine, this is organized as 6 message exchanges per node. The 6 messages have near minimal size and are quickly assembled. As a result, the procedure shown in FIG. 25 requires (excluding the FFT):

$$12 + 6\frac{\Delta_t}{\tau_{pairlist}}$$

communications per step on average. (Above, $\Delta_t$ is the time step and $\tau_{pairlist}$ the interval between pairlist updates.) The amount of data sent (and conversely received) by a node (again, excluding the FFT) per step is:

$$2V_{mm}DN_{bytes\text{-}per\text{-}force} + \frac{1}{2}A_{mm}\lambda DN_{bytes\text{-}per\text{-}particle}\frac{\Delta_t}{\tau_{pairlist}}$$

Above, $V_{mm}$ is the midpoint method import region volume, $A_{mm}$ is the exterior midpoint method import region surface area, $\lambda$ is the average normal particle displacement between pairlist updates and D is the particle density; uniform particle distribution and small normal particle displacement compared to the size of the midpoint method import region have been assumed. For isotropic thermal equal mass particles and a short pairlist interval compared to collisional timescales, $\lambda \sim (2/\pi)^{1/2}(k_B T/m)^{1/2}\tau_{pairlist}$. For a long pairlist interval compared to collisional timescales, $\lambda$ is expected to scale as $\tau_{pairlist}^{1/2}$ due to random walk effects.

Engine Data Structures

Homebox, Local Coordinate System and Clone Buffer

In some embodiments, there may be multiple simulation volumes and each simulation volume is divided into a mesh of homeboxes, for example, with each homebox being a parallelepiped (e.g., a cube). Each homebox is assigned to a node and the 6 homebox faces can be associated with a bi-directional communication link (i.e., −x, +x, −y, +y, −z and +z links) with nodes to which neighboring homeboxes are assigned. The high performance communication primitives described in Kevin J. Bowers et al, "Scalable Algorithms for Molecular Dynamics Simulations on Commodity Clusters," *ACM/IEEE SC* 2006 *Conference* (November 2006) (hereinafter "Bowers 2006") can provide the communication link implementation. Typically, the communications links are arranged to form a periodic mesh of homeboxes.

Each node works in a local coordinate system that is related to the corresponding simulation volume global coordinate system by:

$$\begin{pmatrix} r_x \\ r_y \\ r_z \end{pmatrix}_{global} = \begin{pmatrix} b_{xx} & b_{xy} & b_{xz} \\ b_{yx} & b_{yy} & b_{yz} \\ b_{zx} & b_{zy} & b_{zz} \end{pmatrix}_{local} \begin{pmatrix} r_x \\ r_y \\ r_z \end{pmatrix}_{local} + \begin{pmatrix} c_x \\ c_y \\ c_z \end{pmatrix}_{local}$$

The columns of the 3×3 matrix "b" give the box vectors that describe the node's homebox shape and the 3-vector "c" gives the location of the homebox center in the global coordinate system. FIG. 4 shows a two-dimensional analogy. Two periodic simulation volumes in FIG. 4 have been divided into a 4×4 mesh of square homeboxes. Each homebox is assigned to a node which may have multiple cores. The periodic unit cell shift vectors, homebox mesh and the origin and axes for each coordinate system are shown in FIG. 4.

A three-dimensional homebox consists of all points having all three $r_x$, $r_y$, and $r_z$ coordinates in [−½, ½] in the local coordinate system (i.e., the region consists of the interior of the unit cube and the faces intercepting the negative x, y, and z coordinate axes). The transformation between local coordinate systems on neighboring nodes involves only adding or subtracting the appropriate coordinate components by one. Due to the position representation described later, the transformation between local coordinate systems is exact and reversible for points in the vicinity of several nodes.

The engine ensures calculations assigned to a node only involve positions within or in the vicinity of that node's homebox. Points in the vicinity of a node's homebox form the node's "clone buffer." Generally, the clone buffer contains all points within a given physical distance of the closest point in the homebox. A two-dimensional clone buffer is depicted in FIG. 5. The clone buffer covers the ideal midpoint method import region.

Because calculations assigned to a node involve only points in the vicinity and all points on a node are represented in the local coordinate system, calculations on a node do not have to perform minimum image calculations. Due to the octant maps described later, this is even true when more than one particle image may be present on a node. This increases code performance and reduces code maintenance as no special handling for different simulation topologies is required. Likewise, periodic wrapping calculations are never required. Periodic wrapping is implicitly performed by the transformation of particle positions between local coordinate systems as particles move from node to node; the correct periodic wrapping is implicitly and automatically used for the given homebox mesh connectivity. The use of local coordinates also allows simulations with more exotic boundary conditions to be supported (e.g., arbitrary dynamic triclinic periodic boundary conditions). As a result, signed local normalized coordinates are preferable over the more traditional unsigned global coordinates.

Position Representation

Positions on a node are represented by integer triples ($i_x$, $i_y$, $i_z$). The binary representations of these inters uses an IEEE floating point format:

$$\left( \frac{i_x}{2^{N_{position\text{-}bits}}}, \frac{i_y}{2^{N_{position\text{-}bits}}}, \frac{i_z}{2^{N_{position\text{-}bits}}} \right)$$

That is, positions are represented in a hybrid fixed point/floating point format. Given the local coordinate system described above, $2^{N_{position\text{-}bits}}$ is the number of points representable along each edge of a homebox. Hybrid fixed point/floating point positions may provide one or more of the following advantages:

(1) It allows floating point calculations to be performed bit-level exactly on nodes in the vicinity of nearby positions. As a result, nodes can make decisions consistently based on the results of floating point computations without need for additional communication, increasing code performance. For example, all nodes with copies of two given particles will agree to bit-level on the midpoint location without communication.

(2) It gives extra absolute precision to the position resolution. An extra bit of precision is obtained by using signed coordinates. Further, as more nodes are used, the absolute precision improves for a fixed $N_{position\text{-}bits}$. Positions generally have more absolute precision than the typical and worst case absolute position resolutions of codes that use unsigned global coordinates.

(3) It allows the code precision to be dynamically reconfigured without loss of performance to do numerical studies. Likewise, more consistent and natural values for the coordinates can be used regardless of the code precision. For example, calculations on positions do not have to take into account a code precision dependent scaling factor.

(4) It allows for lattice rounding techniques to be used for more robust numerical simulations of dynamical systems. Specifically, in traditional global coordinate systems, the position precision degrades across the system breaking translation symmetry and floating point non-associativity makes position updates time irreversible.

(5) It allows for code using the engine to avoid slow mixed integer/floating point computations on commodity cores, further increasing performance. Specifically, proper round-to-even of an arbitrary displacement into a hybrid fixed point/floating point displacement can be done very efficiently without multiplications or casting floating point values to and from integers.

FIG. 6 demonstrates a difference between the traditional and engine position representations. The fine vertical ticks denote representable positions along the x-axis (the origin of the coordinate system is indicated by the large fine vertical ticks); the bold horizontal lines denote the homebox and clone buffer assigned to a node and the bold vertical ticks indicate the boundaries of a node's homebox. FIG. 6(a) illustrates unsigned global floating point positions. Minimum image shifts and periodic wrapping explicitly are, in general, required and must be kept consistent with simulation volume topology. FIG. 6(b) illustrates use of signed local hybrid fixed point/floating point positions. Implementations using this representation can have one or more of the following features. All nodes agree on exact position of representable points shared with neighbors. Minimum image shifts and periodic wrapping is implicitly performed and always consistent with global cell and home mesh topology. Physical resolution is constant across system, preserving translation symmetry. Positions updates are reversible, preserving time reversibility. Nodes agree on results of replicated computations, eliminating need for extra communications. Sign bit utilization provides extra position resolution. Position resolution is generally higher in absolute terms and improves as number of nodes used increases. Position resolution is run-time configurable. High performance FPU can be utilized with graceful handling of out-of-range data. Proper round-to-even handling of hybrid positions can be done efficiently.

Records and Caches

Most simulation entities are described by records (e.g., particle record, angle term record, or water constraint record) and each record has a "global id" that identifies what the record describes (e.g., "this particle record describes particle 42"). In some embodiments, each node caches the records it needs to perform assigned calculations and has one local software managed cache for each set of records (e.g., "this cache stores all angle terms needed on this node"). In general, a record with a given global id is present at most once in a cache. However, at "low parallelism," there are situations where multiple images of record with a given global id will be present in a cache (e.g., running the engine on a single node with periodic boundary conditions).

Records are stored contiguously such that if a node has cached $n_{local}$ records, "cache lines" $[0,n_{local})$ will store these records. The local caches are dynamically resized by the engine to accommodate the number of records needed by a node. The index of a local cache line containing a record is that record's "local id". Local caches are organized such that the order of records is unique (this is necessary for integration reversibility in the face of floating point non-associativity). In addition, cache lines are aligned such that SIMD operations like SSE and Altivec can be used on cached records.

Thus, calculations over cached records generally use an array-of-structures data layout, which increases the streamability and spatial locality of memory accesses in calculations. It is also easy to distribute cached records over multiple cores on a node and to use SIMD operations on the records.

Figure 7:
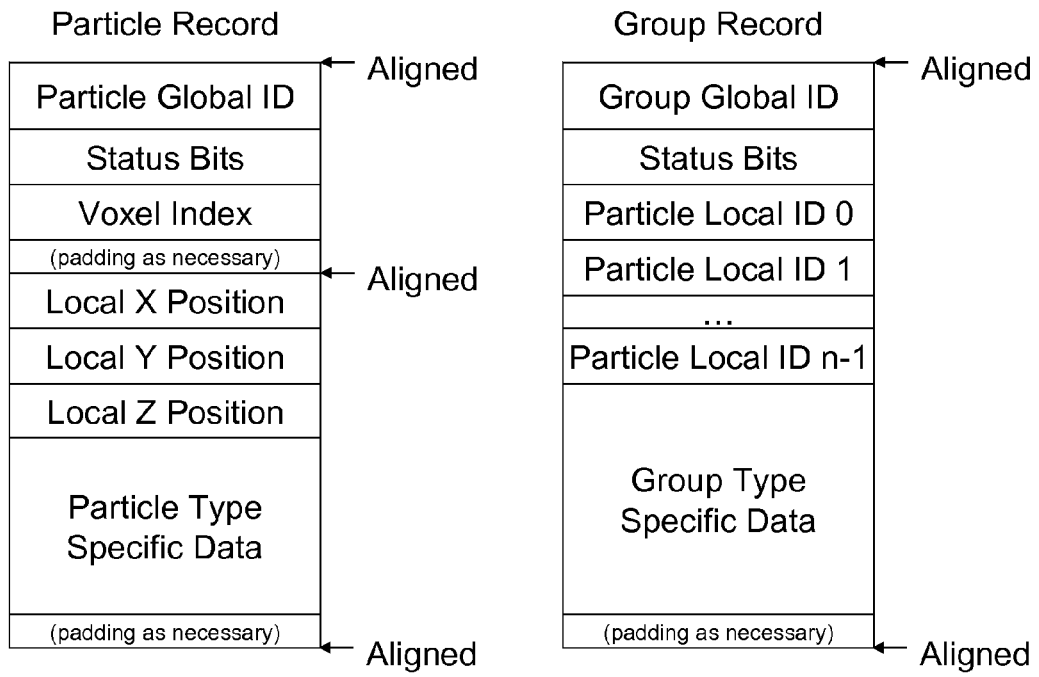
FIG. 7 is a representation of cached record structures.

Within a set of a records (e.g., angle terms), all records have the same layout (e.g., angle term record). In addition, all records share certain characteristics to allow the engine to manage records with different layouts and parallelization requirements simultaneously. There are two broad classes of records. Particle records specify dynamic properties associated with a mobile point in space. A particle record consists of (in this order) global id, status bits, voxel index (described later), local normalized position and record type specific data. The global id and status bits can be thought of as a "cache tag". The engine uses the status bits to decide which records a node needs or should communicate to neighbors. Group records specify properties associated with small fixed sets of nearby particles from the same particle set (e.g., angle terms). A group record consists of (in this order) global id, status bits, group particle local ids and record type specific data. Both particle and group records start with the global id and status bits to allow similar treatment in message processing routines. The number of particles in a group record is determined by the corresponding set of records (e.g., all angle terms have 3 particles). Group records use local particle ids to avoid extra indirection and (at low parallelism) to eliminate the need to determine which set of local particle images to use in computations using that record. FIG. 7 shows the structure of cached records. Particle and group records both start with global id and status bits "cache tags" to allow similar treatment in message processing routines. Particle position is stored in the local coordinate system. This array-of-structures layout increases streamability and spatial locality of memory accesses and makes it easy to distribute records over multiple cores on a node. Records are aligned to allow short vector horizontal and vertical SIMD operations to be performed in computations.

The set of nodes to which a record is distributed is determined by the cache policy of the corresponding set of records. Because the distribution of group records depends on the distribution of particle records, these cache policies form a hierarchy. The cache policies will be described in more detail below.

Queries, Octant Maps and Voxels

Cached records can be found in O(1) operations in 3 different ways. Applications using the engine that do not have a need for fast queries of groups by global id or by spatial location can avoid the additional overhead required for supporting such queries.

(1) By local id (e.g., "return the specific cache line"). This is trivial given the cache organization described previously.

Figure 8:
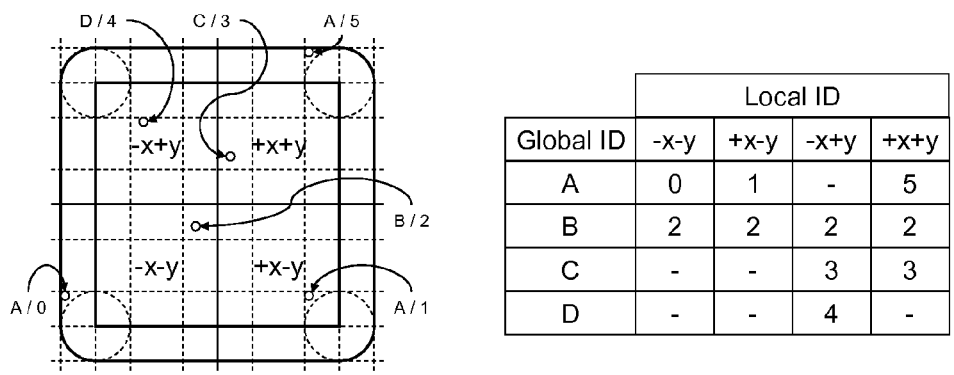
FIG. 8 is a two-dimensional representation of octant maps.

(2) By global id (e.g., "return the cache line that contains the record with a particular global id"). Determining if a record with a particular local id or global id is present on a node is also an O(1) operation. At low parallelism with periodic configurations, multiple records with the same global id may be present in a cache. Octant maps are provided to disambiguate these queries and iterators are also provided to allow applications to process all images of a particle with a given global id on a node. The homebox is divided into eight octants. This is demonstrated in two-dimensions in FIG. 8. For each octant of a homebox, a map from global ids to local ids for all particles within a clone buffer thickness of the octant is provided. This imposes the restriction that at most one image of a particle can be found in the vicinity of a homebox octant. As a result, a node can cache up to eight distinct images of a particle. For each octant of a homebox, a mapping of global ids to local ids is maintained on the node, allowing particles with a particular global id to be found in O(1) operations. This trivially restricts the clone buffer thickness at low parallelism in degenerate cases (e.g., a single homebox assigned an entire periodic unit cell). Simulations with billions of particles on thousands of nodes can use a hash map to support such queries for memory footprint scalability. For simulations with comparatively few particles (millions or less) and/or for simulations parallelized on comparatively few nodes (tens to hundreds), a direct map of global ids to local ids is more practical on the characteristic node.

Figure 9:
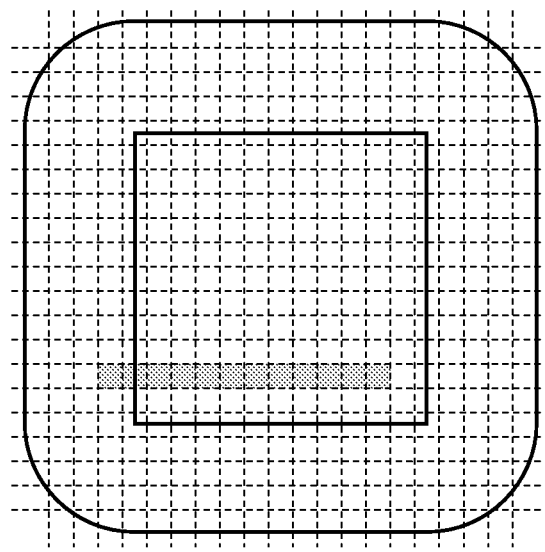
FIG. 9 is a two-dimensional representation of a local voxel mesh

(3) By spatial locality (e.g., "return the cache lines that contain particles within this region of space"). To support this, each particle set divides the homebox and clone buffer into a regular of mesh voxels such that every point is associated with one and only one voxel. Voxel indices are only locally meaningfully; the voxel index of a point on one node has no fixed relation to the voxel index assigned to the same point on a neighboring node. The voxel mesh resolution is typically such that there is approximately one particle per voxel. Cached particles are $O(N_{local})$ sorted by voxel index and the cache partitioning is retained (see "Accelerating a particle-in-cell simulation using a hybrid counting sort," Bowers, *Journal of Computational Physics*, Vol. 173, no. 2, pp. 393-411 (2001), hereinafter "Bowers 2001"). This allows all particles in a range of voxels (as shown in FIG. 9) to be found in O(1) operations. A two-dimensional homebox and clone buffer is divided into a mesh of voxels in FIG. 9. Procedures that need to find particles by spatial location (e.g., pairlist assembly) can rapidly query for all particles in a range of voxels in O(1) operations. The voxel mesh on a node is unrelated to the voxel mesh on neighboring nodes. In the rare case of multiple particles per voxel, all particles within a voxel are sorted by global id to ensure deterministic ordering of cached particles. Deterministic ordering imposes the trivial restriction on the voxel mesh resolution that multiple images of the same particle will never be in the same voxel.

Engine Procedures

Basic Communication Pattern

Figure 10:
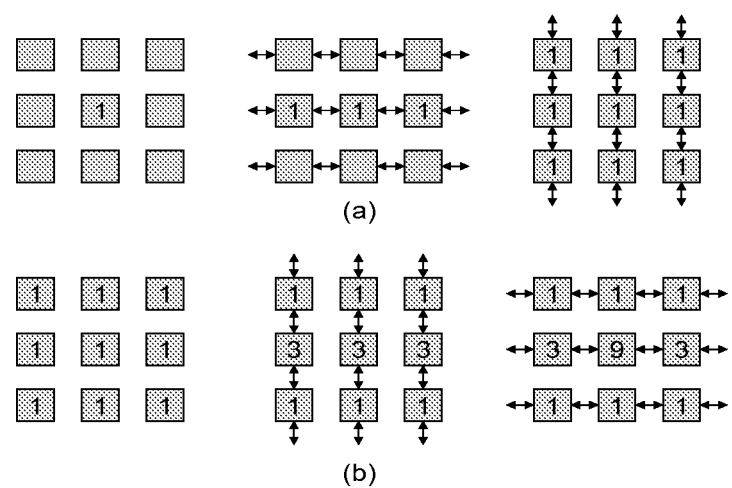
FIG. 10 is a two-dimensional representation of a communication pattern.

In some embodiments, the basic communication pattern used by the engine sends information from a node to all 26 (i.e., =$3^3$−1) nearest neighbors. Because of the extreme latency faced by the engine, this communication is done in 3 sub-rounds with 2 overlapped data exchanges per sub-round. Specifically, in the first sub-round, data is exchanged with the +/−x neighbors along the corresponding communication links, in the second sub-round data is exchanged with the +/−y neighbors, and, in the third sub-round, data is exchanged with the +/−z neighbors (the coalesce operation uses the time-reverse of this pattern). The low level communications in this pattern are very uniformly distributed over the nodes; in practice, each node exchanges exactly one roughly equal sized message with another node in each individual exchange (this property is also holds for the FFT communication pattern). This communication pattern is well-known and has been found to be much more efficient, than, for instance, sending out 26 messages simultaneously. FIG. 10 demonstrates the data flow pattern in two-dimensions. The boxes represent nodes and the arrows represent the exchange of packets between nodes. Note that each exchange involves half the nodes exchanging data with the other half. In typical applications, roughly an equal amount of data is exchanged per node. (a) A value is distributed from the node that owns the value to all its neighbors. (b) A value distributed across all neighbors is reduced to the owner by time-reversing the pattern.

Rather than perform this communication pattern individually for each set of records in an engine operation, to further minimize latency, the engine fuses all communications for each set of records into a single execution of this pattern. To allow for some overlapping of communication and computation, the outgoing messages are sent at the first possible opportunity, the receives from a −link are processed while still waiting for the receives from a +link and the engine starts receiving the 6 messages of the next communication pattern execution before the end of the current communication pattern execution. As such, nodes may begin sending data for the next pattern execution without delay even if other nodes have not started the processing the messages for the next pattern execution.

In some embodiments, the engine implementation restricts the communication pattern to nearest neighbors only. While in other embodiments this communication pattern could be extended further, when used in conjunction with the midpoint method and local parallelization of calculations over cores, this communication restriction does not impose a significant limitation (for example, this could limit the characteristic MD simulation on the characteristic cluster node to 4,096 nodes/16,384 cores). At the same time, this restriction allows very efficient implementations of parallelization bookkeeping to help maintain high scalability.

Migrate Message Assembly

In some embodiments, migrate messages contain all records that need to be transmitted between nodes. To aid with processing and to minimize data volume, these records are organized into sections and tightly packed within each section. Records in a section come from the same record set and have a common origin (e.g., "the records in this section are angle terms from the −x neighbor"). Since global ids are always the first entry of a record, the end of a section is delimited by a sole "invalid global id" (e.g., −1) and has negligible data volume.

Before a migrate step begins, the engine performs a synchronization of all particle data shared between nodes as necessary. Then, for each set of records, a "migrate begin" function is called appropriate for the set's cache policy. The "migrate begin" function removes records no longer necessary on the node from the cache, determines which records should be sent to neighbors and how to embed the record communications in the basic communication pattern (appending copies to outgoing messages as necessary). Finally, it appends an end-of-section delimiter to the outgoing messages. Because group records depend on the underlying particle records, group "migrate begin" functions are called before particle "migrate begin" functions such that group "migrate begin" functions have a guaranteed consistent state for the underlying particle caches.

Figure 11:
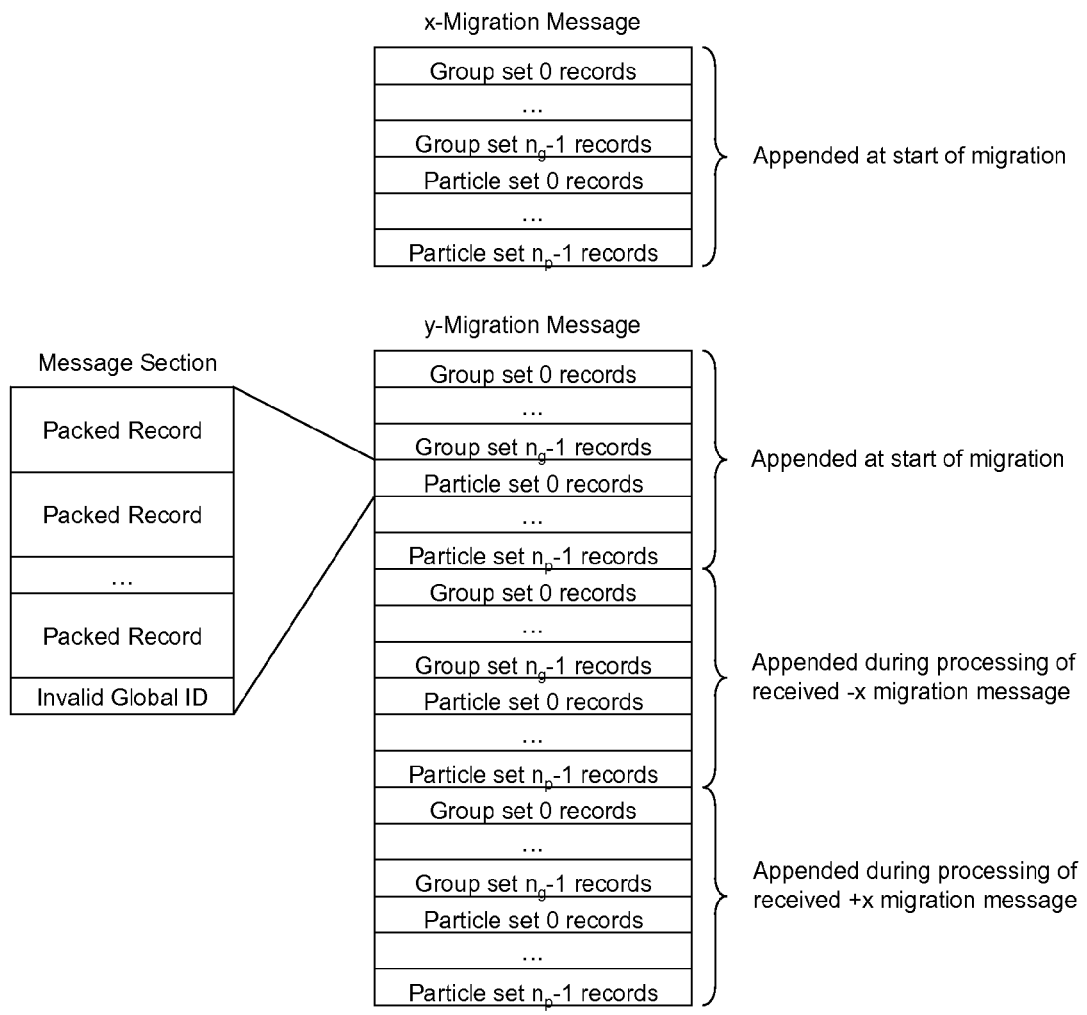
FIG. 11 is a representation of a migrate message structure.

When processing a message received during migrate, for each message section, a "migrate receive" function appropriate for the records in the section is called. The receive function performs any necessary transformations on received records (e.g., transforming particle positions into the local coordinate system) and determines which records it needs to store locally and which to send to additional nodes (appending copies to the remaining outgoing messages as necessary). Finally, it places an end-of-section delimiter on the remaining outgoing messages. Since processing x-receives adds sections to the y- and z-outgoing messages and processing y-receives adds sections to the z-outgoing messages, messages received from the y direction have 3 sections for each set of records and messages received from the z directions have 9 sections for each set of records. (This is far more efficient in local memory data access than passing through local caches multiple times to assemble the messages.) The resulting messages have the structure shown in FIG. 11. There is one collection of sections for each node that may have been a sender of records contributed to the message. Thus, the z-message (not shown) has 9 such collections.

When ending a migrate step, for each set of records, a "migrate end" function is called. The "migrate end" function does remaining bookkeeping necessary for the cached records. Converse to the "migrate begin", the "migrate end" functions for groups are called after the "migrate end" functions for particles such that group "migrate end" functions have a guaranteed consistent state for the underlying particle caches.

In general, store-forward multicast routing is used to minimize the size of messages. For example, if a node needs to send a particle to the −x, −x+y and −x−y+z neighbors, the "migrate begin" will place one copy of the particle in the −x outgoing send even though three copies of the particle are needed at neighbors in that direction. When the −x node processes the received message (from its +x neighbor) in the "migrate receive", it caches a copy of the particle locally and places a copy of the particle into its +y and −y outgoing messages. When the −x+y neighbor processes its received message (from its −y neighbor), it caches a copy of the particle and does not forward the particle further. When the −x−y node processes its received message (from its +y neighbor), it does not cache a copy of the particle but places a copy of the particle into its +z outgoing message. Finally, when the −x−y+z node processes its received message (from its −z neighbor), it caches a copy of the particle. Due to the basic communication pattern xyz-order and the use of store forward multicast in messages, z-messages are slightly larger than y-messages and y-messages are slightly largely than x-messages.

Update and Coalesce Message Assembly

As pairlist assembly and migrate communications are expensive and as particles typically do not move very far in a step, it is advantageous to allow applications to perform these operations infrequently. A mechanism is used to keep all records of a given particle in sync between migrates. Often calculations do not require the entire particle to be updated though. For example, a MD force calculation only requires the positions of all particles to be synchronized as, usually, only the position and velocity data are changing, and the velocity data is not used in the force calculation.

To allow select fields of particles to be synchronized between migrates, the engine maintains gather/scatter communication patterns for each particle set on each node. The gather/scatter patterns list the local ids in order of particles whose data is needed in update and coalesce operations. These patterns are determined in the migrate. When doing an update operation on particles, the engine calls user provided "gatherer" and "scatterer" callback functions that read and write information to outgoing messages. The engine calls these as necessary to assemble the update messages and executes the basic nearest neighbor communication pattern (or the time reverse of it). All communications for different sets of particles are fused into a single execution of the basic communication pattern to minimize internode latency.

Figure 12:
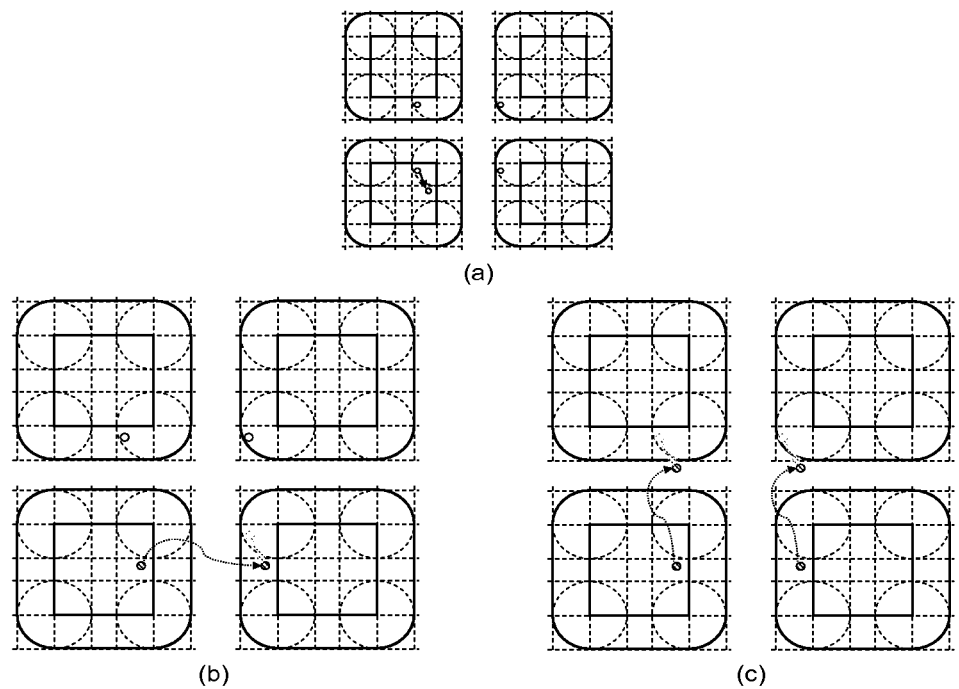
FIG. 12 is a two-dimensional representation of a position update operation.

FIG. 27. shows pseudo-code for a position update gatherer and the matching scatterer. In one embodiment, the engine calls user provided callback functions to perform application specific synchronizations of select particle fields between nodes. Updates for all particle record sets are fused into one basic communication pattern execution and the messages themselves are generally brick-of-bytes with no formatting overhead. The first procedure shown in FIG. 27, indicated (a), is for a position update gatherer. The second procedure shown in FIG. 27, indicated (b), is for a position update scatterer. FIG. 12 shows how the position update proceeds with a two-dimensional example. In FIG. 12 part (a), the Owner changes particle position. In FIG. 12 part (b), Owner gathers position into +x going message; +x neighbor receives message, transforms received position and scatters the result. In FIG. 12 part (c), Owner and x-neighbor gather position into +y going messages; +y and +x+y neighbors receive messages, transform received positions and scatter the results. Store-forward multicast of the update is implicitly encoded in the gather/scatter patterns. Note that a store-forward multicast similar to that used in the migrate operation is used here as well.

Figure 13:
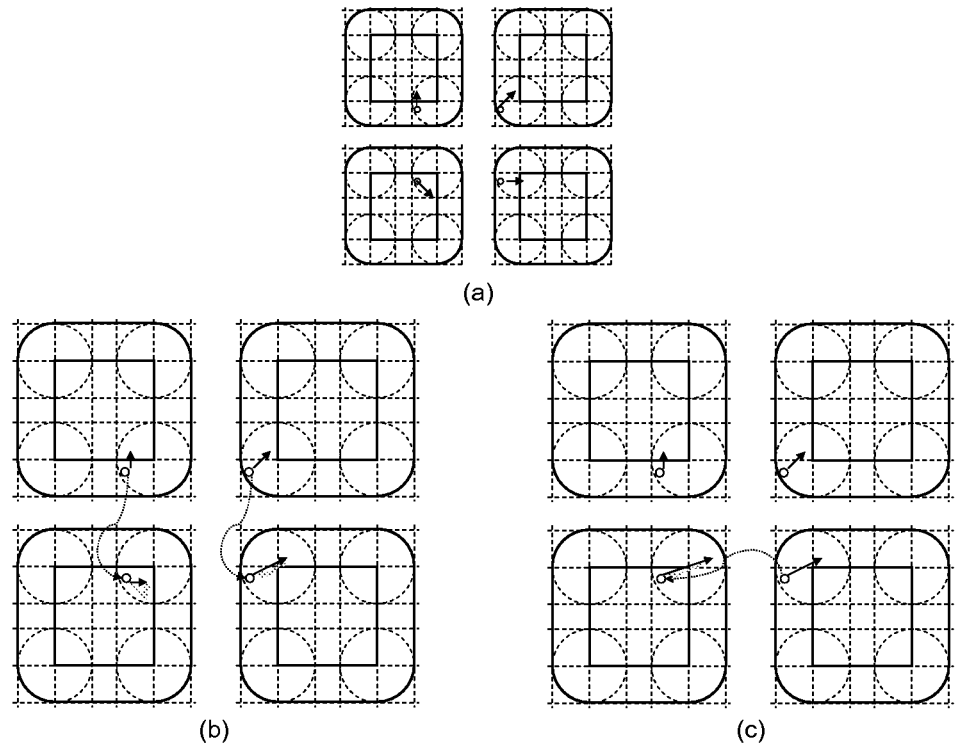
FIG. 13 is a two-dimensional representation of a force coalesce operation.

Coalesce operations use the same gather/scatter patterns, but run in time reversed order. Consistent with time reversal, a coalescing gatherer gathers from particles to which an update operation would scatter and vice versa. FIG. 28 shows pseudo-code for a force coalesce operation. Coalesce operations run a cache update in time-reversed order. As a result, coalesce gatherers gather from particles that would be scattered in an update. The first procedure shown in FIG. 28, indicated (a), is for a Force Coalesce Gatherer. The second procedure shown in FIG. 28, indicated (b), is for a Force Coalesce Scatterer. FIG. 13 shows how a force coalesce operation proceeds with a two-dimensional example. The time-reverse of the update communication pattern is used. At operation end, the owner has the complete force. In FIG. 13 part (a), partial forces on particle have been computed on several nodes. In FIG. 13 part (b), +x and +x+y neighbors gather partial forces into −y going messages; owner and +x neighbor receive messages and reduce received forces locally. In FIG. 12 part (c), +x neighbor gathers updated partial force into −x going message; owner receives message and reduces received force locally. Note that only the owner has the final result after a coalesce operation. There is a variant with lower latency for strictly commutative operations that coalesces and updates simultaneously.

The resulting messages for update and coalesce operations are generally "brick-of-bytes"; no formatting overhead is imposed by the engine. Applications have the freedom to synchronize the absolute minimum amount of data between nodes to perform their computations, reducing internode data volume.

Particle Cache Policies

In some embodiments, the engine provides two cache policies for particles: the clone policy and the un-rounded clone policy. These policies ensure that each node has a copy of all particles in the node's homebox and clone buffer following a migrate. The only difference between the two policies is the shape of the clone buffer region. In the un-rounded clone policy, the clone buffer region is a hollow parallelepiped that tightly surrounds the homebox of specified thickness along the local x, y and z directions. In the clone policy, the hollow parallelepiped of the un-rounded clone policy is rounded in the local coordinate system at the edges and corners to reduce bandwidth as shown in FIG. 5. Generally, in a manner that is compatible with the midpoint method, the clone buffer is configured to contain all points within a given physical distance of the closest corresponding point in the homebox. These policies are very similar in operation so only the clone policy is detailed below.

Immediately after a migrate, a node "owns" all particles that reside in its homebox. After each migrate, there is one and only one owner for a particle with a specific global id. A node also has a copy (a "clone") of all particles that are in the surrounding clone buffer region. Usually, a node has only one copy of a particle with a given global id. However, at low parallelism, multiple copies of the same particle (e.g., different periodic images) may be present on a node. The octant maps, voxel indexing data structures and the gather/scatter communication patterns have been updated to reflect the new distribution of particles.

Figure 14:
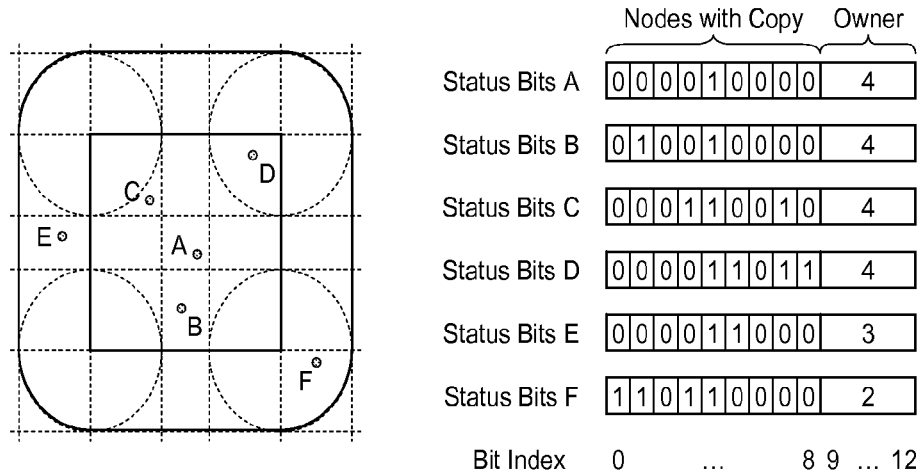
FIG. 14 is a two-dimensional representation of particle locations and a table of associated status bits

Ownership of a particle indicates that the node always has current particle data. 5 particle status bits indicate which neighbor is the particle owner (e.g., the −x−z neighbor is the owner). 27 particle status bits indicate which neighbors of the owner have a copy (e.g., the +x and +x+z neighbors of the owner have a clone of the particle). Conveniently, the status bits fit in a 32-bit processor word (i.e., the size of an integer). A two-dimensional example of the status bits is shown in FIG. 14. Owner status bits indicate the relative neighbor that owns this particle record. The "nodes with copy" bit field gives nodes relative to the owner that have a copy of this particle record. By virtue of how particle positions are represented, all nodes can compute the status bits of a local particle without need for communication. That is, because different nodes can compute bitwise identical numeric results, that status bits can be computed based on arithmetic inequalities (e.g., corresponding to presence in defined spatial regions) without the risk that numerical differences (e.g., rounding or summation order effects) will result in different values of the status bits being computed at different nodes. (Note that bit 4 is always set in this two-dimensional example because the owner always has a copy).

When it is time to perform a migrate, the application synchronizes particle data as necessary. Then the engine redistributes the particles and updates all bookkeeping data structures. By restricting the maximum particle displacement between migrates to less than the clone buffer thickness, a node is guaranteed to have a copy of all particles within its homebox at the start of a migrate. Using this property and the restriction that a local clone buffer can only overlap with homeboxes on neighboring nodes, particles never need to be sent to or received from more than nearest neighbors.

Figure 15:
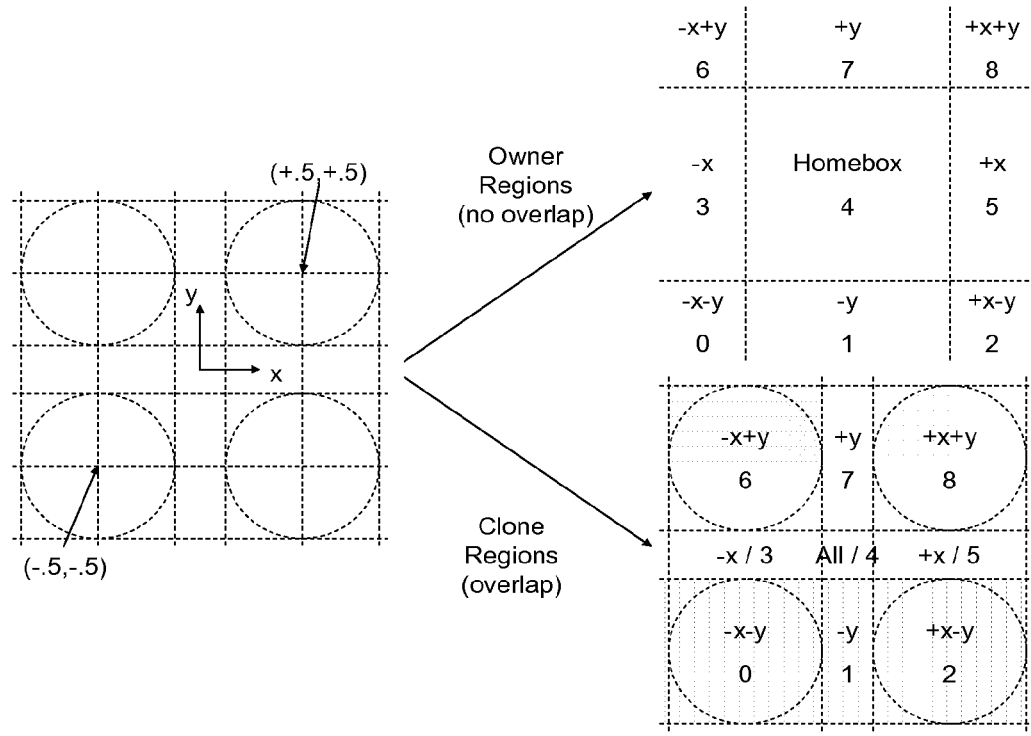
FIG. 15 is a two-dimensional representation of status bit computation regions and relative local node indexing.

During a migrate, new status bits for a particle can be computed efficiently. Each point in the vicinity of a homebox is associated with the regions shown in FIG. 15. Owner regions indicate which neighbor's homebox contains a point and do not overlap. Clone regions indicate which neighbors are in the vicinity of a point. Clone regions overlap. Owner regions identify which homebox in the vicinity of the node contains the point (e.g., "this point is in the −x neighbor homebox") and do not overlap. Clone regions are used to identify which points are in the vicinity of various neighbors (e.g., "this point is in the vicinity of the −x neighbor, −y neighbor and −x−y neighbors"). These overlap each other and owner regions. Though the clone regions have rounded shapes, inclusion in clone regions can be computed very quickly with tests of the form:

$$n_x\left(\frac{r_x - n_x/2}{d_x}\right)^2 + n_y\left(\frac{r_y - n_y/2}{d_y}\right)^2 + n_z\left(\frac{r_z - n_z/2}{d_z}\right)^2 < 1$$

where $r_x$, $r_y$ and $r_z$ specify the position in a local coordinate system, $n_x$, $n_y$ and $n_z$ (in $\{-1,0,1\}$) specify the particular clone region (e.g., "points in the vicinity of the −x neighbor") and $d_x$, $d_y$ and $d_z$ specify the clone buffer thicknesses along each direction. Note that because transformations between local coordinate systems are exact, these clone regions tests can be done in floating point without concern that round-off error will cause nodes to disagree on which regions a shared point belongs. By encoding the owner regions in 5 bits and the clone regions in 27 bits analogous to the status bits, the region computation of a particle position in the (new) owner local coordinate system yields exactly what the status bits should be for a particle at the end of a migrate. This is shown in FIG. 29, Particle Status Bit Computation. All the if-tests above can be performed with branchless conditional move operations in assembly and the for-loops can be completely unrolled. All nodes that need a copy of the particle are guaranteed to produce bit-level identical results.

During a migrate, using the new and old status bits, determining which nodes need a copy of a particle but do not have one, whether a particle is needed on a node, whether a particle should be part of a scatter or gather message and so forth can be reduced to a handful of assembly operations. For example, a particle is still needed on a node if it is within that node's homebox or clone buffer. This is equivalent to stating that a particle is needed locally if it in clone region $(-n_x,-n_y,-n_z)$ of the neighbor $(n_x,n_y,n_z)$ that owns it. In pseudo code:

test bit number 26-status_bits.owner in status_bits

In practice, this amounts to roughly 4 assembly operations on typical sized machine words. Note the restriction that the clone buffer only overlaps nearest neighbor nodes is used to simplify the logic and greatly accelerate these computations.

FIG. 30 shows the particle clone policy migrate begin procedure. The routing and bulk of the outgoing communications for the particles are assembled in a single pass. Likewise, unnecessary particles are flushed without communication but the cache is kept contiguous in memory. All memory access is streaming memory access (except octant map clearing). Note that particles are in sync before the migrate begins on a particle set. Likewise, the status bits are stale but consistent with the current particle distribution. The particle voxel indices are stale. Some particles may no longer be needed locally and other needed particles may be missing. This operation costs $O(N_{local})$. The routing and bulk of the communication messages have been assembled in a single pass through the particles. All memory access (except octant map clearing) is a streaming memory access and locally cached particles are kept contiguous in memory. Particles no longer needed locally have been flushed without communication. Copies of a particle appended to an outgoing message use the status bits of a particle to indicate the particle multicast routing. Note that the octant maps have been cleared in this function.

The particle clone policy migrate receive procedure is given in FIG. 31. Note that the local cache is not reprocessed to assemble subsequent receives. This uses pure streaming memory operations. The total number of particles sent (and conversely received) by a node is roughly:

$$\frac{1}{2}A_{mm}\lambda D$$

($A_{mm}$, $\lambda$ and D were defined in the introduction), assuming uniform particle density, isotropic particle motion and small particle displacements compared to clone buffer thickness.

The processing cost of this function scales similarly. No random memory access is used by this function. Computation is traded for bandwidth in this procedure as the new particle status bits could be sent from the owner in addition to the store-forward multicast routing. If this were done, instead of re-computing the status bits of particles a node stores locally, the node would receive both the status bits and the routing information. It would then update the owner field in the status bits before storing. The engine does not do this due to the fact that the additional inter-node data volume cost plus the status bit update cost minus the status bit re-computation cost for a clone buffer surface area scaling computation is negligible.

Once all the migrate messages have been processed, all the particles needed on a node are present and the status bits current. The particle migrate end procedure sets up the octant maps, voxel lookup and cache update gather/scatter patterns. First, the voxel indexing data structures are setup in $O(N_{local})$ operation based on Bowers 2001 to finalize the local ids of cached particles. Then the cache gather scatter patterns are computed and the global ids to local ids mappings are inserted into the octant maps (the octant maps were scalably cleared by the migrate begin function).

Figure 16:
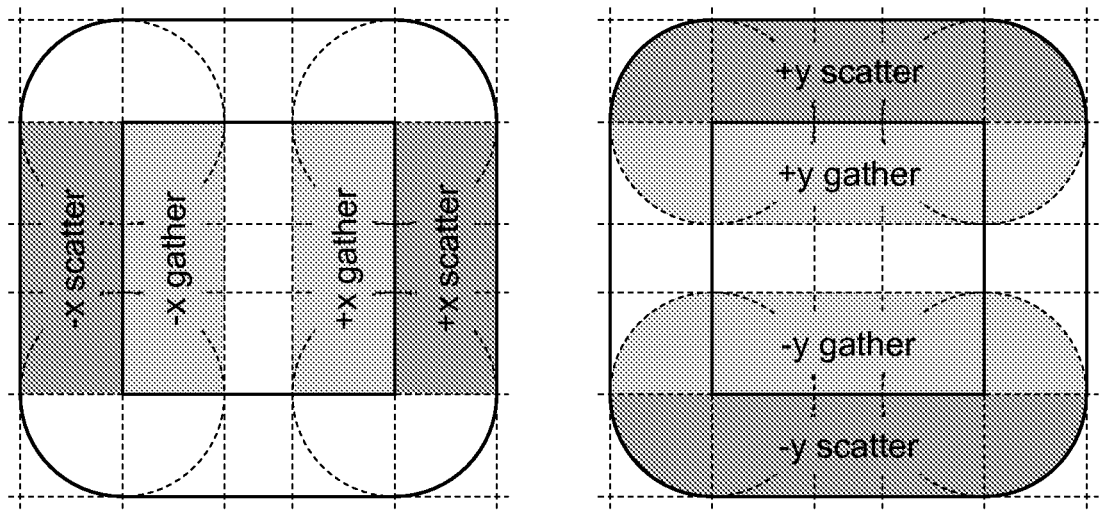
FIG. 16 are two-dimensional representations of a homebox with particle clone policy gather and scatter regions.

Each cache update message is associated with a non-overlapping portion of the homebox and clone buffer. These regions are matched such that the "+x gather region" on a node contains the same particles as the "−x scatter region" on the +x neighbor. Since all nodes have the particles they need at this point with current information, neighbors will agree on the set of particles in matching gather/scatter regions at this point without communication. For example, a node and +x neighbor will agree on the set of particles in the node's+x gather region and the +x neighbor's −x scatter region. Using particle global ids (and positions in the case of multiple particle images in the same gather/scatter region), the nodes can also determine a unique order for all particles in matching regions without communication. Testing whether a particle is in a gather/scatter region only requires examining the particle status bits and can be done in a handful of assembly operations. FIG. 16 shows a two-dimensional example of gather scatter regions, assuming the communication sub-rounds go in xy order. These regions are used to rapidly assemble gather/scatter communication patterns. After all migrate messages have been processed, nodes agree on the set of particles in matching gather/scatter regions and can determine a unique ordering without communication. The test for being in a gather/scatter region can be done looking only at the particle status bits in a handful of assembly operations. The resulting messages implicitly encode a store-forward multicast routing like that used in a migrate.

The resulting procedure for the migrate end is shown in FIG. 32. Given that the number of voxels typically scales as $N_{local}$, this procedure costs roughly $O(N_{local})$. Note that global id ties in the gather/scatter sorting process in general only occur at low parallelism in the y- and z-gather/scatter patterns.

Figure 17:
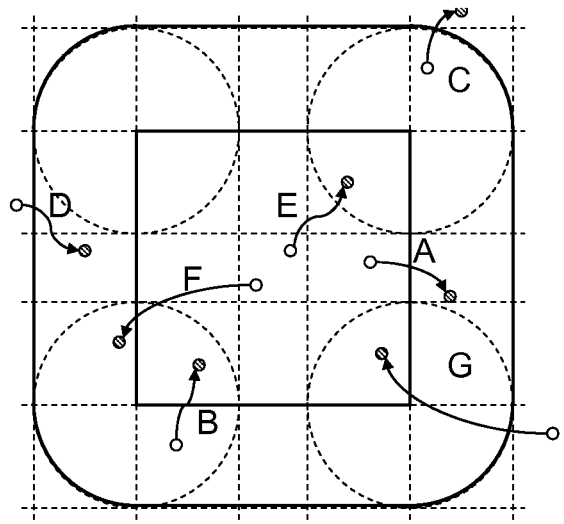
FIG. 17 is a two-dimensional representation of a homebox with particle clone policy migrate operations.

How select cases for a particle migrate are handled is shown in FIG. 17. Arrows indicate the displacement of a particle image between migrates. Select cases: (A) +x neighbor takes ownership from local node, no communication necessary; (B) Local node takes ownership from −y neighbor, no communication necessary; (C) Flushed from local node, no communication necessary; (D) −x neighbor adds to +x going migrate message and the local node stores a copy on receipt; (E) Local node sends particle to +x,+y,+x+y neighbors via store-forward multicast, neighbors store a copy on receipt; (F) and (G) Forbidden, particle has moved more than a clone buffer thickness. Assuming (as is typical) particles move a negligible fraction of the clone buffer thickness between migrates, data volume sent and received by a node scales as the clone buffer exterior surface area. No particles are sent at all if particles do not move between migrates. Note that minimal particles are sent; if particles have not moved between migrates, no particles are sent at all.

Group Cache Policies

Anchor Points and Compatible Images

Group cache policies are very similar to particle cache policies. This is made possible by implicitly associating each group with a single position analogous to the position of a particle. This point is the group "anchor point". The anchor point is used to determine which node owns the group, which node is responsible for sending copies to neighbors, which particle octant map is capable of converting a group stored in terms of global particle ids to a compatible set of local particle ids and so forth.

Figure 18:
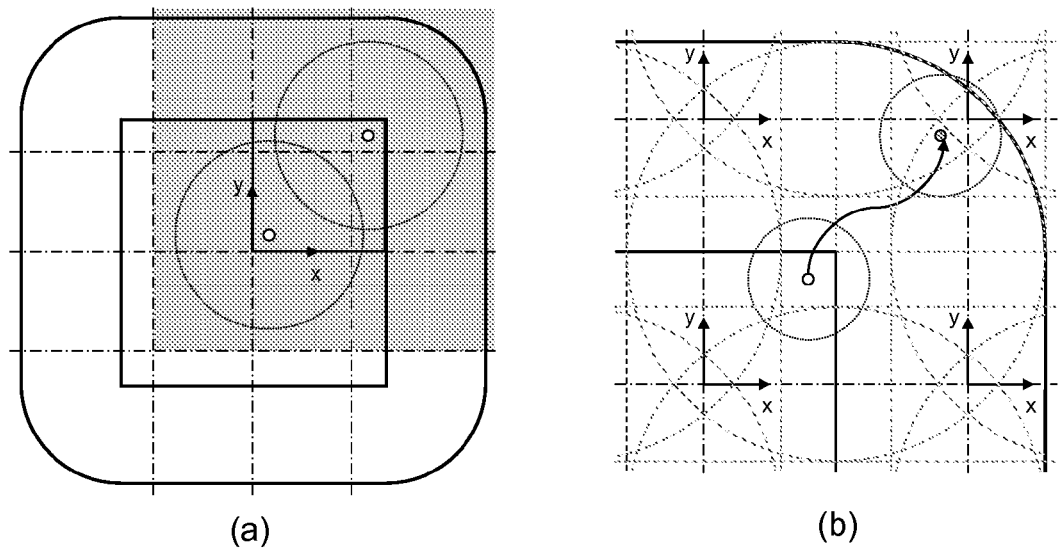
FIG. 18 is a two-dimensional representation of a group anchor point
Figure 19:
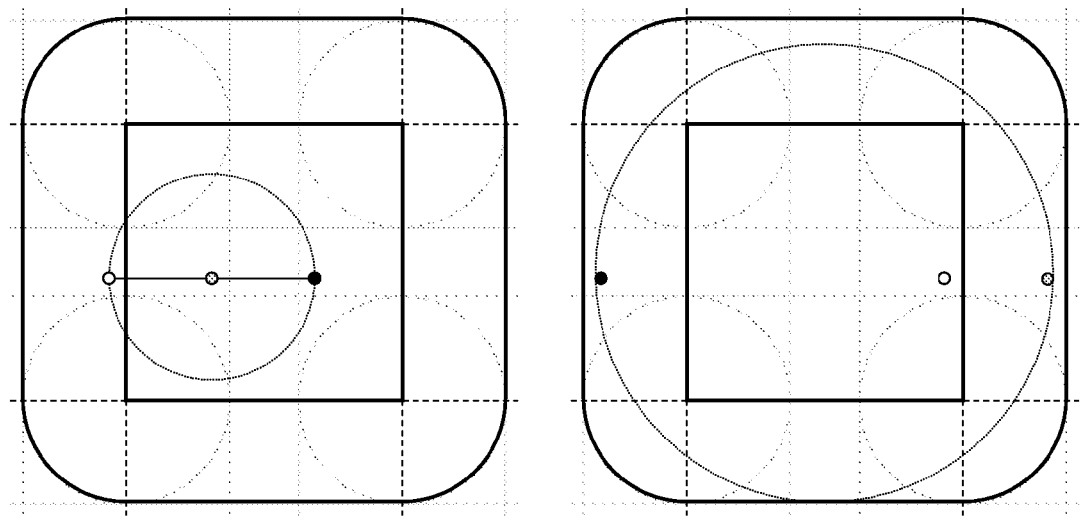
FIG. 19 is a two-dimensional representation of compatible particle images in a group.

All particles in a group lie within, at most, a clone buffer thickness of the anchor point. As a result, groups always involve compatible particle images and the particle octant map corresponding to the anchor point is always capable of mapping the group particle ids from global ids to appropriate local ids as shown in FIG. 18. Each group has an "anchor point" analogous to particle position. All particles in a group must lie within a minimum clone buffer thickness of the anchor point, as shown in FIG. 18(a). Like the particle position, the group anchor point has the restriction that it may not move more than a clone buffer thickness between migrates, as shown in FIG. 18(b). The group anchor point has the additional restriction that it may not move more than half a homebox edge thickness between migrates. The latter restriction insures that the local octant of the anchor point on the current owner is always trivially related to the local octant of the anchor on any neighbor that may have copies sent to it during the next migrate (simulation with very thick clone buffers shown in FIG. 18). Incompatible groups can be detected as groups with particles that are further away than a clone buffer thickness from the anchor point as shown in FIG. 19. FIG. 19 demonstrates a two-dimensional periodic system partitioned into a mesh with 2 homeboxes along x. The first node, shown in FIG. 19 on the left, and the second node, shown in FIG. 19 on the right, both have a complete set of particles images for a group. However, only the node on the left has a compatible set of images (i.e., all particles in the group come from the "same" unit cell). The distance from the anchor point to the furthest particle exceeds the clone buffer thickness in an incompatible set of images.

Like the position of a particle, the group anchor point has the restriction that it may not move more than a clone buffer thickness between migrates. The group anchor point has the additional restriction that it may not move more than half a homebox edge between migrates. The latter restriction insures that the local octant of an anchor point on the current owner is always trivially related to the local octant of that anchor point on any neighbor that may have copies sent to it during the next migrate.

Some embodiments of the engine support 4 group cache policies: the midpoint policy, the replicate policy, the anchor policy and the ensured policy. The policies differ on how the anchor point is defined and the set of nodes to which groups are distributed. The midpoint policy and the replicate policy are the most often used in applications.

Group Midpoint Policy

A group parallelized via the midpoint policy is stored on the node which contains the group midpoint at the time of last migrate. As such, a midpoint group is present in the system on exactly one node and which is a useful property for calculations that should be performed exactly once (e.g., MD bond term calculations). The group midpoint is, for example, the center of the smallest sphere which contains all the particles. As another example, the arithmetic mean of the particle coordinates is a good approximation for most applications (and exact for groups with fewer than three particles). All particles within a midpoint group should be within the minimum physical clone buffer thickness of the midpoint. Since midpoint groups are assigned to one and only one node, midpoint group record type specific data can be modified freely. The anchor point of a midpoint group is the midpoint.

Figure 20:
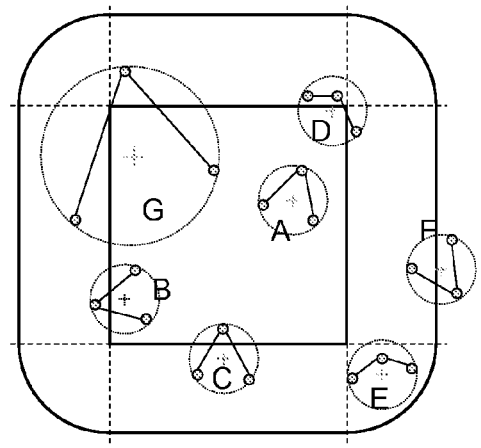
FIG. 20 is a two-dimensional representation of a homebox demonstrating group midpoint policies.

FIG. 20 shows how midpoint groups are distributed in select cases using a two-dimensional example. A group parallelized via the midpoint policy is stored on the node which contained the group midpoint at the last migrate. Select two-dimensional analogy cases are shown in FIG. 20 (the anchor point/group midpoint is shown by the cross-hairs): (A) assigned to local node; (B) assigned to local node, local node does not own all particles; (C) assigned to −y neighbor, local node does not own all particles; (D) assigned to local node, local node owns no particles in group; (E) assigned to +x−y neighbor, local node owns no particles in group; (F) assigned to +x neighbor, could not be assigned to local node; (G) assigned to local node, largest possible size.

Group Replicate Policy

A particle owned by a node and in a replicate group will be in a compatible image of that group exactly once on that node. Conversely, a copy of a replicate group is present on a node for each complete compatible set of particle images on that node that contain at least one owned particle. Since particles in this group may be owned by different nodes, copies of the group may exist on several nodes (at low parallelism, there may even be multiple group images present on a single node). The replicate policy is ideal for calculations that update a group of particles simultaneously (e.g., MD constraint terms) as each node can perform the update for all particles it owns without need for additional synchronization (due to the position representation, replicated calculations in general can be performed bit level identically). No two particles within a replicate group may be further apart than the clone buffer thickness; this is stricter than the midpoint policy. By convention, the group anchor point is the first group particle position though any group particle position would suffice. As such, the owner of a replicate group is the owner of the first particle. Replicate group application specific data should only be modified in a way guaranteed to produce bit-level consistent results on all nodes that have a copy of the group.

Figure 21:
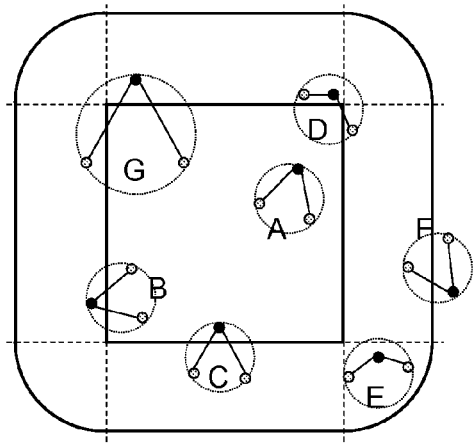
FIG. 21 is a two-dimensional representation of a homebox demonstrating group replicate policies.

FIG. 21 shows how replicate groups are distributed in select cases using a two-dimensional example. A particle owned by a node and in a replicate group will be in a compatible copy of that group exactly once on that node. Since group particles may be owned by different nodes, copies of the group record may exist on several nodes (at low parallelism, there may even be multiple copies of the group record present on a single node). Select two-dimensional analogy cases are shown in FIG. 21 (anchor point is the particle in black): (A) assigned to local node; (B) assigned to local node and −x node; (C) assigned to local node and −y neighbor; (D) assigned to +x and +y neighbors; local node does not own any particles; (E) assigned to +x−y neighbor, local node owns no particles in group; (F) assigned to +x neighbor, could not be assigned to local node; (G) assigned to local node, −x and +y neighbors, largest possible size.

Group Anchor Policy

A group parallelized by the anchor policy is stored on the node that owns the first particle in the group. As such, the group is present exactly once in the system. The anchor policy can be used to specify additional properties of select particles and for calculations that use a group of particles to update the state of a single particle (e.g., MD Drude particle algorithms). No particle in an anchor group may be more than a minimum clone buffer thickness from the first particle in the group (this is more strict than the midpoint policy but less strict than the replicate policy). The anchor policy is similar to the midpoint policy in that the group is assigned to one and only one node and group application specific data can be modified freely. The anchor policy can also be thought of as a degenerate case of a generalized replicate policy in which groups are replicated on nodes that own select group particles. Like the replicate policy, the anchor point of an anchor group is the first group particle position.

Figure 22:
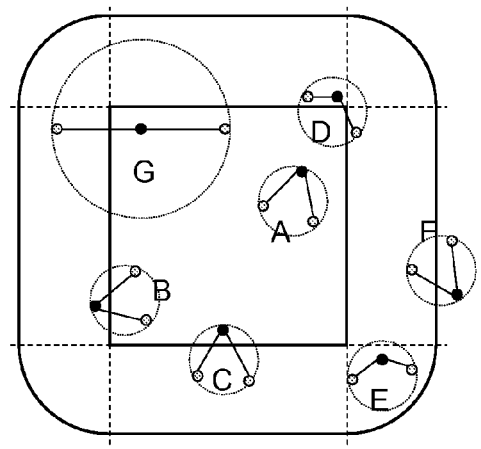
FIG. 22 is a two-dimensional representation of a homebox demonstrating group anchor policies.

FIG. 22 shows how anchor groups are distributed in select cases using a two-dimensional example. A group parallelized by the anchor policy is stored on the node that owns the first particle in the group. Select two-dimensional analogy cases are shown in FIG. 22 (anchor point is the particle in black): (A) assigned to local node; (B) assigned to −x neighbor; (C) assigned to local node; (D) assigned to +y neighbor; (E) assigned to +x−y neighbor; (F) assigned to +x neighbor, could not be assigned to local node; (G) assigned to local node, largest possible size.

Group Ensured Policy

A copy of a group parallelized by the ensured policy is present for each set of compatible group particle images on a node. The ensured policy is used for dynamic load balancing algorithms as calculations based on ensured groups can be performed on any node capable of performing the calculation. Ensured groups have the same size restriction and anchor point as midpoint groups. As such, the owner of an ensured group is the node whose homebox contains the group midpoint. Like the replicate policy though, group application specific data should only be modified if done so in a way guaranteed to produce consistent results for all copies of that group.

Figure 23:
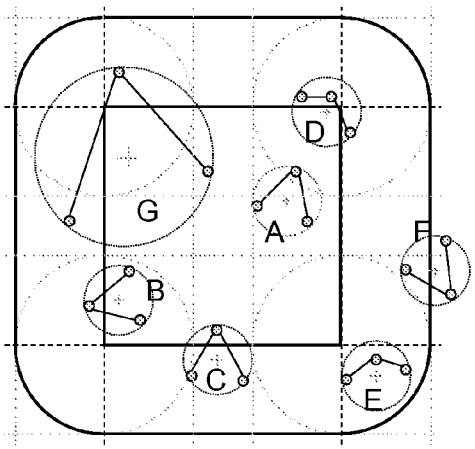
FIG. 23 is a two-dimensional representation of a homebox demonstrating group ensured policies.

FIG. 23 shows how ensured groups are distributed in select cases using a two-dimensional example. One image of a group parallelized by the ensured policy is present for each set of compatible group particle images on a node. Select two-dimensional analogy cases are shown in FIG. 23 (the anchor point/group midpoint is shown by cross-hairs): (A) assigned to local node and +x neighbor; (B) assigned to local node, −x, −y and −x−y neighbors; (C) assigned to local node and −y neighbor; (D) assigned to local node, +x, +y and +x+y neighbors; (E) assigned to local node, +x, −y, +x−y neighbors; (F) assigned to +x neighbor, could not be assigned to local node; (G) assigned to local node only, largest possible size.

Migrate Procedures

The implementations for the group cache policies are very similar and share a great deal in common with the particle cache policies. Only the replicate policy procedures will be detailed.

Before migrate begins, the application has synchronized particle data as necessary and when a group migrate begin function is called, migrate on the particle set underlying this group has not yet started. Thus, all the particles needed for locally cached groups are still available on this node and in sync. Groups are in sync but some groups may no longer be needed on this node while others may be missing. The status bits of groups and particles are stale but consistent with the current group and particle distribution. The group replicate policy migrate begin procedure is shown in FIG. 33. This procedure costs $O(N_{local})$ and uses bit operations very similar to the particle clone policy. While migrate is underway, the group is stored in terms of particle global ids and the local octant of the anchor point on the current owner is preserved to allow the group to be mapped into new particle local ids at migrate completion. No holes are created in the cache and most memory operations are streaming (the particle lookups are necessarily random access). While a migrate is underway, groups are stored in terms of particle global ids as particle local ids are reassigned during the migrate process and no relationship exists between the local ids of particles on different nodes. The preserved octant information is used at migrate end to determine the correct set of images to use when converting the group back to local ids.

The group replicate policy migrate receive function is likewise very similar to the particle clone policy migrate receive function. All group policies use the receive procedure shown in FIG. 34. This uses pure streaming memory operations. The octant transformation is a trivial bit mask given the restrictions on anchor point movement between migrates. Particle local ids have not been finalized at this point, so particle global ids cannot be transformed to particle local ids yet. The octant information can be transformed to the local octant with a trivial bit mask under the easily satisfied restrictions given for anchor point movement.

After all messages have been processed and particle caches finalized by their migrate end functions, the migrate end functions for the groups are called. These functions need to convert groups back to particle local ids and arrange them in memory to insure a deterministic ordering. This is given in FIG. 35. This is called after the particle migrate end functions to convert back to local ids before completing the migrate. This operation costs $O(N_{local})$. The restriction on anchor point movement, preserving the old octant during a migrate and the particle octant map ensure the right set of particles images needed for the group can be found in O(1) operations out of potentially thousands of sets to consider.

Like the particle clone policy, no groups are sent at all if the underlying particles have not moved between migrates.

There is some redundant computation above. For example, the new owner of a particle in a replicate group is computed in the replicate group policy migrate begin and in the particle clone policy migrate begin. Like the redundancies in the particle clone policy, the operation count benefits of exploiting these redundancies are negligible compared to increased memory traffic, increased communications, and/or increased implementation complexity.

Pairlist Procedures

To support calculations over all pairs of particles within a cutoff distance, the engine provides rapid pairlist assembly procedures. The pairlist procedures used by the engine support finding all nearby pairs between particles from the same particle set, finding all nearby pairs between particles in different particle sets, assembling redundant pairlists (i.e., a pair i-j is considered distinct from a pair j-i) and assembling pairlists with select pairs excluded. Some embodiments of the engine have the implementation restriction that exclusions can only be done for pairlists involving pairs from the same set of particle records. This description explains, as an example, assembling non-redundant pairlists between particles from the same set with exclusions.

Pairs are assigned to the node at the pair midpoint. The pairlist procedures require that the pairlist cutoff distance be less than twice the minimum physical clone buffer thickness. In this case, the set of pairs assigned to a node can be assembled without additional communication immediately after migrate. Namely, each node constructs a local pairlist with all pairs that:

(1) Are not excluded
(2) Have a separation less than the cutoff distance
(3) Have a midpoint within the node's homebox Due to the restriction on cutoff distance, each node is guaranteed to have all particle information necessary to process these pairs. Further, since the homeboxes cover the simulation volume completely and without overlap, each non-excluded nearby pair in the system is guaranteed to occur exactly once in exactly one local pairlist (assuming a convex simulation volume).

Since only non-redundant pairs should be considered, the set of local pairs can be structured such that the first particle ("i-particle") in the pair has a local id greater than the second particle ("j-particle"). Thus, conceptually, the local pairlist could be assembled as shown in FIG. 36. The position representation used by the engine ensures that all nodes will agree on the distance and midpoint calculations. The position representation used by the engine ensures all nodes agree on the results of the tests in FIG. 36 without communication. This procedure is slow but it can be greatly sped up by taking advantage of the O(1) spatial query capabilities of particle sets. Alternative implementations of the pairlist procedure make use of conventional programming optimizations.

The pairlist template stores all pairs of voxels in the local voxel mesh that contain at least one pair of points (one point drawn from each voxel) within the pairlist cutoff distance and at least one pair of points whose midpoint is within the local homebox. The voxel pairs are stored in a compressed format: for each voxel, all voxels with which it is paired with a lower or equal index are encoded as a set of voxel ranges in increasing order and saved in the template (e.g., "voxel 147 is paired with voxels 10-15, 34-56 and 90-147"). This encoding compresses the set of voxel pairs by roughly three-quarters over a more standard sparse matrix storage format and reduces the number of spatial queries necessary during pairlist assembly. As a result, during pairlist assembly, only candidate pairs highly likely to be included in the pairlist are tested and these candidate pairs can be found very quickly. The pairlist template is usually only computed at the start of a simulation, but, it can be computed very efficiently in $O(N_{local,voxel})$ operations. FIG. 24 demonstrates the pairlist template using a two-dimensional example. The pairlist template stores all pairs of voxels in that contain at least one pair of points within the pairlist cutoff distance and at least one pair of points with a midpoint within the homebox. The voxel pairs are stored in a compressed format: for each voxel, all voxels with which it is paired with a lower or equal index are encoded as a set of ranges in increasing order. The pairlist template is usually computed once at the start of a simulation, but, it can be computed very efficiently in $O(N_{local,voxel})$ operations.

Exclusions are stored as a set of groups under the midpoint policy. The dynamic load balanced midpoint ensured method described in Bowers 2006 uses the ensured policy. Because pairs and exclusions are both assigned to nodes by midpoint, locally cached exclusions are the minimal set needed for local pairlist assembly. This is more scalable in space and time than the more common practice of storing a copy of all exclusion data on each node. So that exclusions for an i-particle can be found quickly during local pairlist assembly, cached exclusions are first converted into an "exclusion pairlist" such that all non-redundant exclusions with an i-particle can be found in O(1) operations. Since the local pairlist has the property that i-particle local ids are greater than the j-particle local ids, the conversion procedure needs to ensure the exclusion pairlist has the same property. FIG. 37 shows the local exclusion conversion procedure. Cached exclusions are converted into a local "exclusion pairlist" to facilitate rapid pairlist assembly. Assuming, as is typical, the number of exclusions in the system is proportional to the number of particles, this procedure is $O(N_{local})$. Since the local exclusion pairlist is derived from groups parallelized via the midpoint policy, exclusions correctly only exist between compatible particle images.

Assuming, as is typical, the number of exclusions in the system is proportional to the number of particles, this procedure is $O(N_{local})$.

Given the voxel of an i-particle, promising candidate j-particles can be rapidly found by examining all particles in the corresponding pairlist template voxel ranges (these ranges can be found in O(1) operations). Given the sorting of particles by voxel index and the pairlist template voxel range organization, candidate j-particles already have a lower local id than the i-particle (except for candidates in the same voxel as the i-particle) and are considered in monotonically increasing local id order. This forms the heart of the local pairlist assembly in FIG. 38. This assembles the local pairlist in $O(N_{local,pairs})$ operations. (The engine actually uses a multiple core load balanced version of this procedure and computes how to distribute pairs among multiple cores as the load balance required for assembling a pairlist is not necessarily optimal for computations using the pairlist.) In the inner loop, the tests given above can be seen. (The additional redundant pair test in the inner loop handles the special case of multiple interacting particles in the same voxel.) Due to the fine voxel mesh resolution and pairlist template, most candidate j-particles pass all tests. Hence, the number of candidates tested is comparable to the number of actual local pairs for a given i-particle.

Usually, most particles paired with particle i will also be paired with particle i+1. This, and the fact that the j-particles for a given i-particle occur in monotonically increasing order, gives a high degree of spatial and temporal data locality to local pairlist assembly and computations using the local pairlist. Both involve quasi-streamed memory accesses (Hilbert voxel indexing schemes could improve this slightly).

The "exclusion bit field" used in the procedure is notable. Generally, there are more pairs than exclusions and a comparatively expensive test in the inner loop based on either the cached exclusions or local exclusion pairlist is less than ideal. To minimize the cost of inner loop exclusion testing, the procedure uses an $N_{local}$ wide bit field. Before testing i-particles against candidate j-particles, for each j-particle that should be excluded, the corresponding bit is set in the exclusion bit field. As a result, inner loop exclusion testing requires an O(1) single bit test. After testing all the candidate j-particles, the exclusion bit field is cleared by zeroing the bits that were set (this is more efficient than clearing the whole bit field).

U.S. Provisional Application No. 60/909,037 filed Mar. 30, 2007, is incorporated by reference for the purpose of providing descriptions for example embodiments. In the case of a conflict between the description provide above and the incorporated material, the present description should govern. It is to be understood that the foregoing is intended to illustrate and not to limit the scope of the invention. Other embodiments are within the scope of the following claims:

What is claimed is:

1. A method for distributed computation of multiple body interactions in a region using a plurality of processing modules, each of the processing modules being associated with a respective corresponding portion of the region, the method comprising establishing a plurality of coordinate frames of reference, each processing module of the plurality of processing modules corresponding to one of the plurality of coordinate frames of reference, and maintaining information for bodies in the region, including at each of the processing modules, maintaining information for bodies in the portion of the region corresponding to the processing module according to the coordinate frame of reference corresponding to the processing module, wherein at least some of the bodies have information maintained concurrently at multiple different processing modules according to different coordinate frames of reference, said method further comprising, for each of a plurality of groups of bodies for which information for each of the bodies in the group is maintained at each of multiple processing nodes using multiple different coordinate frames of reference, performing a computation that depends on locations of the bodies in the group resulting in an identical result at each of the processing modules.

2. The method of claim 1, wherein performing the computation that depends on locations of the bodies comprises evaluating a numerical inequality.

3. The method of claim 1, wherein performing the computation that depends on locations of the bodies comprises computing an interaction between the bodies.

4. A method for distributed computation of multiple body interactions in a region using a plurality of processing modules, each of the processing modules being associated with a respective corresponding portion of the region, the method comprising establishing a plurality of coordinate frames of reference, each processing module of the plurality of processing modules corresponding to one of the plurality of coordinate frames of reference, and maintaining information for bodies in the region, including at each of the processing modules, maintaining information for bodies in the portion of the region corresponding to the processing module according to the coordinate frame of reference corresponding to the processing module, wherein at least some of the bodies have information maintained concurrently at multiple different processing modules according to different coordinate frames of reference, and wherein maintaining information for bodies in the portion of the region corresponding to a processing module according to the coordinate frame of reference corresponding to the processing module includes using a representation of location information with a first spatial precision for bodies in the portion of the region associated with the processing module, the representation not supporting said first precision for the complete region using a single coordinate frame of reference.

5. The method of claim 4, wherein the representation comprises an integer representation, the integer representation not supporting representation of locations in the complete region using the coordinate frame of reference associated with the processing node.

6. The method of claim 5, wherein the representation comprises a floating point representation with an exponent part and a fractional part, the integer representation of location information using the fractional part of the floating point representation.

7. A method for distributed computation of multiple body interactions in a region using a plurality of processing modules, each of the processing modules being associated with a respective corresponding portion of the region, the method comprising establishing a plurality of coordinate frames of reference, each processing module of the plurality of processing modules corresponding to one of the plurality of coordinate frames of reference, and maintaining information for bodies in the region, including at each of the processing modules, maintaining information for bodies in the portion of the region corresponding to the processing module according to the coordinate frame of reference corresponding to the processing module, and passing information for bodies from a first of the processing modules to a second of the processing modules, the information for the bodies being maintained at the first processing module according to a first coordinate frame of reference, including transforming the information for the bodies from the first coordinate frame of reference to a second coordinate frame of reference for maintaining at the second of the processing modules wherein at least some of the bodies have information maintained concurrently at multiple different processing modules according to different coordinate frames of reference.

8. The method of claim 7, further comprising, for each of a plurality of groups of bodies for which information for each of the bodies in the group is maintained at each of multiple processing nodes using multiple different coordinate frames of reference, performing a computation that depends on locations of the bodies in the group resulting in an identical result at each of the processing modules.

9. The method of claim 8, wherein performing the computation that depends on locations of the bodies comprises evaluating a numerical inequality.

10. The method of claim 8, wherein performing the computation that depends on locations of the bodies comprises computing an interaction between the bodies.

11. The method of claim 7, wherein maintaining information for bodies in the portion of the region corresponding to a processing module according to the coordinate frame of reference corresponding to the processing module includes using a representation of location information with a first spatial precision for bodies in the portion of the region associated with the processing module, the representation not supporting said first precision for the complete region using a single coordinate frame of reference.

12. The method of claim 11, wherein the representation comprises an integer representation, the integer representation not supporting representation of locations in the complete region using the coordinate frame of reference associated with the processing node.

13. The method of claim 12, wherein the representation comprises a floating point representation with an exponent part and a fractional part, the integer representation of location information using the fractional part of the floating point representation.

14. The method of claim 7, further comprising performing a plurality of computations, each computation being associated with a group of bodies, information for each of at least some of the groups of bodies being maintained at multiple of the processing modules, wherein performing the computation associated with the group of bodies includes selecting a single of the multiple processing modules for performing the computation by independently using information for the group of bodies maintained at each of the multiple processing modules.

15. A method for distributed computation of multiple body interactions in a region using a plurality of processing modules, each of the processing modules being associated with a respective corresponding portion of the region, the method comprising establishing a plurality of coordinate frames of reference, each processing module of the plurality of processing modules corresponding to one of the plurality of coordinate frames of reference, and maintaining information for bodies in the region, including at each of the processing modules, maintaining information for bodies in the portion of the region corresponding to the processing module according to the coordinate frame of reference corresponding to the processing module, wherein at least some of the bodies have information maintained concurrently at multiple different processing modules according to different coordinate frames of reference, said method further comprising performing a plurality of computations, each computation being associated with a group of bodies, information for each of at least some of the groups of bodies being maintained at multiple of the processing modules, wherein performing the computation associated with the group of bodies includes selecting a single of the multiple processing modules for performing the computation by independently using information for the group of bodies maintained at each of the multiple processing modules.

16. Non-transitory Computer-readable media encoded with computer-readable software comprising instructions for causing a processing system to perform distributed computation of multiple body interactions in a region using a plurality of processing modules, each of the processing modules being associated with a respective corresponding portion of the region, wherein the method of computation comprises: establishing a plurality of coordinate frames of reference, each processing module of the plurality of processing modules corresponding to one of the plurality of coordinate frames of reference; and maintaining information for bodies in the region, including at each of the processing modules, maintaining information for bodies in the portion of the region corresponding to the processing module according to the coordinate frame of reference corresponding to the processing module; and passing information for bodies from a first of the processing modules to a second of the processing modules, the information for the bodies being maintained at the first processing module according to a first coordinate frame of reference, including transforming the information for the bodies from the first coordinate frame of reference to a second coordinate frame of reference for maintaining at the second of the processing modules; wherein at least some of the bodies have information maintained concurrently at multiple different processing modules according to different coordinate frames of reference.

17. The computer-readable media of claim 16, wherein the method of computation further comprises, for each of a plurality of groups of bodies for which information for each of the bodies in the group is maintained at each of multiple processing nodes using multiple different coordinate frames of reference, performing a computation that depends on locations of the bodies in the group resulting in an identical result at each of the processing modules.

18. The computer-readable media of claim 17, wherein performing the computation that depends on locations of the bodies comprises evaluating a numerical inequality.

19. The computer-readable media of claim 17, wherein performing the computation that depends on locations of the bodies comprises computing an interaction between the bodies.

20. The computer-readable media of claim 16, wherein maintaining information for bodies in the portion of the region corresponding to a processing module according to the coordinate frame of reference corresponding to the processing module includes using a representation of location information with a first spatial precision for bodies in the portion of the region associated with the processing module, the representation not supporting said first precision for the complete region using a single coordinate frame of reference.

21. The computer-readable media of claim 20, wherein the representation comprises an integer representation, the integer representation not supporting representation of locations in the complete region using the coordinate frame of reference associated with the processing node.

22. The computer-readable media of claim 21, wherein the representation comprises a floating point representation with an exponent part and a fractional part, the integer representation of location information using the fractional part of the floating point representation.

23. The computer-readable media of claim 16, wherein the method further comprises performing a plurality of computations, each computation being associated with a group of bodies, information for each of at least some of the groups of bodies being maintained at multiple of the processing modules, wherein performing the computation associated with the group of bodies includes selecting a single of the multiple processing modules for performing the computation by independently using information for the group of bodies maintained at each of the multiple processing modules.

* * * * *